United States Patent [19]
Nesvadba et al.

[11] Patent Number: 5,773,631
[45] Date of Patent: Jun. 30, 1998

[54] 3-ARYLBENZOFURANONES AS STABILIZERS

[75] Inventors: Peter Nesvadba; Samuel Evans, both of Marly, Switzerland; Christoph Kröhnke, Breisach, Germany; Jürg Zingg, Reinach, Switzerland

[73] Assignee: Ciba Specialty Chemicals Corporation, Tarrytown, N.Y.

[21] Appl. No.: 606,896

[22] Filed: Feb. 26, 1996

Related U.S. Application Data

[62] Division of Ser. No. 304,468, Sep. 12, 1994, Pat. No. 5,516,920.

[30] Foreign Application Priority Data

Sep. 17, 1993 [CH] Switzerland ................ 2810/93-7

[51] Int. Cl.$^6$ ................................... C07D 409/04
[52] U.S. Cl. ................. 549/43; 549/58; 549/60
[58] Field of Search ................ 549/60, 43, 58

[56] References Cited

U.S. PATENT DOCUMENTS

| | | |
|---|---|---|
| 4,325,863 | 4/1982 | Hinsken et al. . |
| 4,338,244 | 7/1982 | Hinsken et al. . |
| 5,175,312 | 12/1992 | Dubs et al. . |
| 5,322,525 | 6/1994 | Rembold et al. . |

FOREIGN PATENT DOCUMENTS

| | | |
|---|---|---|
| 415887 | 3/1991 | European Pat. Off. . |
| 589839 | 3/1994 | European Pat. Off. . |
| 591102 | 4/1994 | European Pat. Off. . |
| 4202276 | 8/1992 | Germany . |
| 2044272 | 10/1980 | United Kingdom . |
| 2252325 | 8/1992 | United Kingdom . |
| 2257140 | 1/1993 | United Kingdom . |
| 2257141 | 1/1993 | United Kingdom . |
| 2267088 | 11/1993 | United Kingdom . |
| 2267490 | 12/1993 | United Kingdom . |
| 2267491 | 12/1993 | United Kingdom . |
| 8001566 | 8/1980 | WIPO . |

OTHER PUBLICATIONS

Ullmans Encyklopadie dertechnischen Chemie, vol. 13, pp.85–94 (1977).
Houben Weyl, Metpden der Organischen Chemie vol. VI/IC p. 1030 (1976).
Monatshefte für Chemie 99 pp. 2223–2226 (1968).
M.Julia et al., Bull Soc. Chim. FR 1965, 2175.
J. Org. Chem. S7, pp. 362–366 (1992).
Monatshefte für Chemie 99 pp. 990–994 (1968).
Beilstein, E III/IV, 18 pp. 154–166 (1975).
Beilstein 18, 17 (1934).
Organikum, pp. 402–408 (1986).
Organikum pp. 186–191 (1986).
J. Chem. Soc. Chem. Commun. 1989, 1353.
J. Chem. Soc. Chem. Commun. 1980, 851.
T. Yamaguchi, Applied Catalysis, 61 (1990) pp. 1–25.
J. Morran, et al., Bull. Soc. Chim. FR. 1979, pp. 583–591.
Derwent Abst. 94–103409/13 of EP 589, 839, (1994).
Derwent Abst. 94–111456/14 of EP 591,102, (1994).

*Primary Examiner*—Robert W. Ramsuer
*Attorney, Agent, or Firm*—Michele A. Kovaleski; Victoria M. Malia

[57] ABSTRACT

The invention described novel compounds of formula

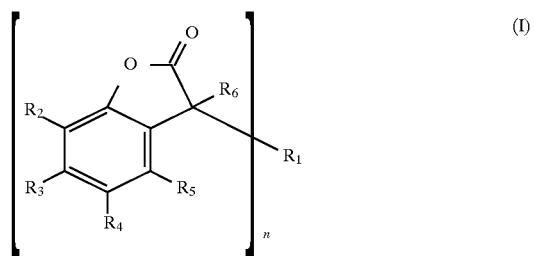

wherein the general symbols are as defined in claim 1, as stabilisers for protecting organic materials, in particular polymers and lubricants, against thermal, oxidative or light-induced degradation.

6 Claims, No Drawings

3-ARYLBENZOFURANONES AS STABILIZERS

This is a divisional of Ser. No. 08/304,468, filed Sep. 12, 1994 now U.S. Pat. No. 5,516,920.

The present invention relates to novel 3-arylbenzofuranones, to compositions comprising an organic material, preferably a polymer or a lubricant, and to the novel stabilisers, as well as to the use thereof for stabilising organic materials against oxidative, thermal or light-induced degradation.

Individual 3-arylbenzofuran-2-ones are known in the literature and have been described, inter alia, by J. Morvan et al., Bull. Soc. Chim. Fr. 1979, 583.

The use of some 3-phenyl-3H-benzofuran-2-ones as stabilisers for organic polymers is disclosed, inter alia, in U.S. Pat. No. 4,325,863; U.S. Pat. No. 4,338,244 and U.S. Pat. No. 5,175,312.

It has now been found that a selected group of 3-arylbenzofuran-2-ones is particularly suitable for use as stabilisers for organic materials that are susceptible to oxidative, thermal or light-induced degradation.

Accordingly, the invention relates to compounds of formula I

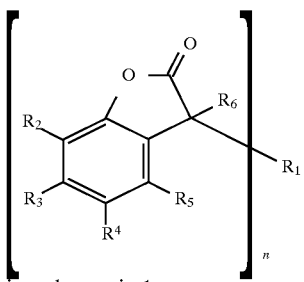

wherein, when n is 1, $R_1$ is naphthyl, phenanthryl, anthryl, 5,6,7,8-tetrahydro-2-naphthyl, 5,6,7,8-tetrahydro-1-naphthyl, thienyl, benzo[b]thienyl, naphtho[2,3-b]thienyl, thiathrenyl, dibenzofuryl, chromenyl, xanthenyl, phenoxathlinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, terphenyl, fluorenyl or phenoxazinyl, each unsubstituted or substituted by $C_1$–$C_4$alkyl, $C_1$–$C_4$alkoxy, $C_1$–$C_4$alkylthio, hydroxy, halogen, amino, $C_1$–$C_4$alkylamino, phenylamino or di($C_1$–$C_4$alkyl)amino, or $R_1$ is a radical of formula II

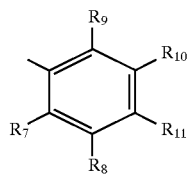

and when n is 2, $R_1$ is phenylene or naphthylene which is unsubstituted or substituted by $C_1$–$C_4$alkyl or hydroxy; or is —$R_{12}$—X—$R_{13}$—, $R_2$, $R_3$, $R_4$ and $R_5$ are each independently of one another hydrogen, chloro, hydroxy, $C_1$–$C_{25}$alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di($C_1$–$C_4$alkyl)amino, $C_1$–$C_{25}$alkanoyloxy, $C_1$–$C_{25}$alkanoylamino, $C_3$–$C_{25}$alkenoyloxy, $C_3$–$C_{25}$alkanoyloxy which is interrupted by oxygen, sulfur or

$C_6$–$C_9$cycloalkylcarbonyloxy, benzoyloxy or $C_1$–$C_{12}$alkyl-substituted benzoyloxy; with the proviso that, when $R_2$ is hydrogen or methyl, $R_7$ or $R_9$ is not hydroxy or $C_1$–$C_{25}$alkanoyloxy; each pair of substituents $R_2$ and $R_3$ or $R_3$ and $R_4$ or $R_4$ and $R_5$, together with the linking carbon atoms, forms a benzene ring; $R_4$ is additionally —$(CH_2)_p$—$COR_{15}$ or —$(CH_2)_q$OH, or when $R_3$, $R_5$ and $R_6$ are hydrogen, $R_4$ is additionally a radical of formula III

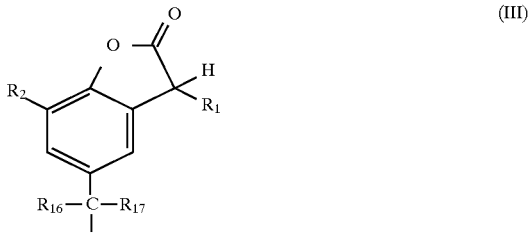

wherein $R_1$ is as defined above for n=1, $R_6$ is hydrogen or a radical of formula IV

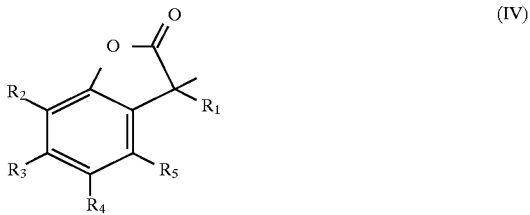

in which $R_4$ is not a radical of formula III and $R_1$ is as defined above for n=1, $R_7$, $R_8$, $R_9$ and $R_{10}$ are each independently of one another hydrogen, halogen, hydroxy, $C_1$–$C_{25}$alkyl, $C_2$–$C_{25}$alkyl which is interrupted by oxygen, sulfur or

$C_1$–$C_{25}$alkoxy, $C_2$–$C_{25}$alkoxy which is interrupted by oxygen, sulfur or

$C_1$–$C_{25}$alkylthio, $C_3$–$C_{25}$alkenyl, $C_3$–$C_{25}$alkenyloxy, $C_3$–$C_{25}$alkynyl, $C_3$–$C_{25}$alkynyloxy, $C_7$–$C_9$phenylalkyl, $C_7$–$C_9$phenylalkoxy, unsubstituted or $C_1$–$C_4$alkyl-substituted phenyl; unsubstituted or $C_1$–$C_4$alkyl-substituted phenoxy; unsubstituted or $C_1$–$C_4$alkyl-substituted $C_5$–$C_8$cycloalkyl; unsubstituted or $C_1$–$C_4$alkyl-substituted $C_5$–$C_8$cycloalkoxy; $C_1$–$C_4$alkylamino, di-($C_1$–$C_4$alkyl)amino, $C_1$–$C_{25}$alkanoyl, $C_3$–$C_{25}$alkanoyl which is interrupted by oxygen, sulfur or

$C_1$–$C_{25}$alkanoyloxy, $C_3$–$C_{25}$alkanoyloxy which is interrupted by oxygen, sulfur or

$C_1$–$C_{25}$alkanoylamino, $C_3$–$C_{25}$alkenoyl, $C_3$-$C_{25}$alkenoyl which is interrupted by oxygen, sulfur or

$C_3$–$C_{25}$alkenoyloxy, $C_3$–$C_{25}$alkenoyloxy which is interrupted by oxygen, sulfur or

$C_6$–$C_9$cycloalkylcarbonyl, $C_6$–$C_9$-cycloalkylcarbonyloxy, benzoyl or $C_1$–$C_{12}$alkyl-substituted benzoyl; benzoyloxy or $C_1$–$C_{12}$alkyl-substituted benzoyloxy;

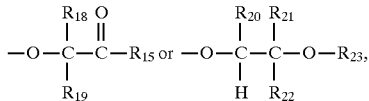

or also in formula II each pair of substituents $R_7$ and $R_8$ or $R_8$ and $R_{11}$, together with the linking carbon atoms, forms a benzene ring, $R_{11}$ is hydrogen, $C_1$–$C_{25}$alkyl, $C_1$–$C_{25}$alkylthio, $C_3$–$C_{25}$alkenyl, $C_3$–$C_{25}$alkynyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; $C_1$–$C_4$alkylamino, di($C_1$–$C_4$alkyl)amino, $C_1$–$C_{25}$alkanoyl, $C_3$–$C_{25}$alkanoyl which is interrupted by oxygen, sulfur or

$C_1$–$C_{25}$alkanoylamino, $C_3$–$C_{25}$alkenoyl, $C_3$–$C_{25}$alkenoyl which is interrupted by oxygen, sulfur or

$C_6$–$C_9$cycloalkylcarbonyl, benzoyl or $C_1$–$C_{12}$alkyl-substituted benzoyl; with the proviso that at least one of $R_7$, $R_8$, $R_9$, $R_{10}$ or $R_{11}$ is not hydrogen, $R_{12}$ and $R_{13}$ are each independently of the other unsubstituted or $C_1$–$C_4$alkyl-substituted phenylene or naphthylene, $R_{14}$ is hydrogen or $C_1$–$C_8$alkyl, $R_{15}$ is hydroxy,

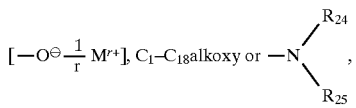

$R_{16}$ and $R_{17}$ are each independently of the other hydrogen, $CF_3$, $C_1$–$C_{12}$alkyl or phenyl, or $R_{16}$ and $R_7$, together with the linking carbon atom, form a $C_5$–$C_8$cycloalkylidene ring which is unsubstituted or substituted by 1 to 3 $C_1$–$C_4$alkyl groups;

$R_{18}$ and $R_{19}$ are each independently of the other hydrogen, $C_1$–$C_4$alkyl or phenyl, $R_{20}$ is hydrogen or $C_1$–$C_4$alkyl, $R_{21}$ is hydrogen, unsubstituted or $C_1$–$C_4$alkyl-substituted phenyl; $C_1$–$C_{25}$alkyl, $C_2$–$C_{25}$alkyl which is interrupted by oxygen, sulfur or

$C_7$–$C_9$phenylalkyl which is unsubstituted or substituted in the phenyl moiety by 1 to 3 $C_1$–$C_4$alkyl groups; $C_7$–$C_{25}$phenylalkyl which is interrupted by oxygen, sulfur or

and which is unsubstituted or substituted in the phenyl moiety by 1 to 3 $C_1$–$C_4$alkyl groups; or $R_{20}$ and $R_{21}$, together with the linking carbon atoms, form a $C_5$–$C_{12}$cycloalkylene ring which is unsubstituted or substituted by 1 to 3 $C_1$–$C_4$alkyl groups;

$R_{22}$ is hydrogen or $C_1$–$C_4$alkyl, $R_{23}$ is hydrogen, $C_1$–$C_{25}$alkanoyl, $C_3$–$C_{25}$alkenoyl, $C_3$–$C_{25}$alkanoyl which is interrupted by oxygen, sulfur or

$C_2$–$C_{25}$alkanoyl which is substituted by a di($C_1$–$C_6$alkyl) phosphonate group; $C_6$–$C_9$cycloalkylcarbonyl, thenoyl, furoyl, benzoyl or $C_1$–$C_{12}$alkyl-substituted benzoyl;

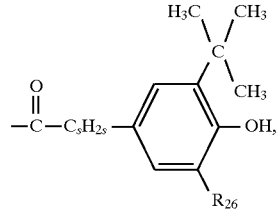

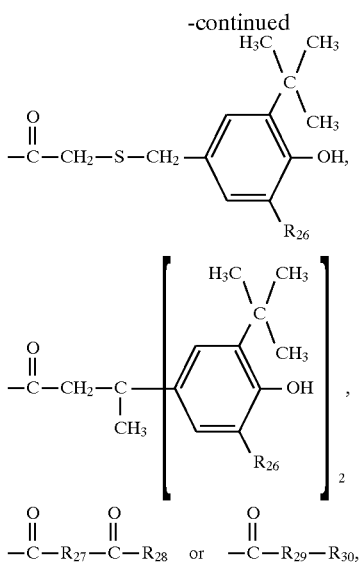

$R_{24}$ and $R_{25}$ are each independently of the other hydrogen or $C_1$–$C_{18}$alkyl, $R_{26}$ is hydrogen or $C_1$–$C_8$alkyl, $R_{27}$ is a direct bond, $C_1$–$C_{18}$alkylene, $C_2$–$C_{18}$alkylene which is interrupted by oxygen, sulfur or

$C_2$–$C_{18}$alkenylene, $C_2$–$C_{20}$alkylidene, $C_7$–$C_{20}$phenylalkylidene, $C_5$–$C_8$cycloalkylene, $C_7$–$C_8$bicycloalkylene, unsubstituted or $C_1$–$C_4$alkyl-substituted phenylene,

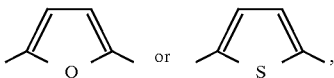

$R_{28}$ is hydroxy,

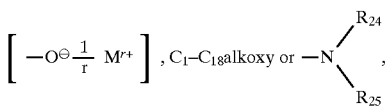

$R_{29}$ is oxygen, —NH— or

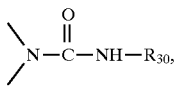

$R_{30}$ is $C_1$–$C_{18}$alkyl or phenyl,
$R_{31}$ is hydrogen or $C_1$–$C_{18}$alkyl,
M is a metal cation of valency r,
X is a direct bond, oxygen, sulfur or —$NR_{31}$—,
n is 1 or 2,
p 0, 1 or 2,
q is 1, 2, 3, 4, 5 or 6,
r is 1, 2 or 3, and
s is 0, 1 or 2.

Naphthyl, phenanthryl, anthryl, 5,6,7,8-tetrahydro-2-naphthyl, 5,6,7,8-tetrahydro-1-naphthyl, thienyl, benzo[b]thienyl, naphtho[2,3-b]thienyl, thiathrenyl, dibenzofuryl, chromenyl, xanthenyl, phenoxathlinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, terphenyl, fluorenyl or phenoxazinyl, each unsubstituted or substituted by $C_1$–$C_4$alkyl, $C_1$–$C_4$alkoxy, $C_1$–$C_4$alkylthio, hydroxy, halogen, amino, $C_1$–$C_4$alkylamino, phenylamino or di($C_1$–$C_4$alkyl)amino, will typically be 1-naphthyl, 2-naphthyl, 1-phenylamino-4-naphthyl, 1-methylnaphthyl, 2-methylnaphthyl, 1-methoxy-2-naphthyl, 2-methoxy-1-naphthyl, 1-dimethylamino-2-naphthyl, 1,2-dimethyl-4-naphthyl, 1,2-dimethyl-6-naphthyl, 1,2-dimethyl-7-naphthyl, 1,3-dimethyl-6-naphthyl, 1,4-dimethyl-6-naphthyl, 1,5-dimethyl-2-naphthyl, 1,6-dimethyl-2-naphthyl, 1-hydroxy-2-naphthyl, 2-hydroxy-1-naphthyl, 1,4-dihydroxy-2-naphthyl, 7-phenanthryl, 1-anthryl, 2-anthryl, 9-anthryl, 3-benzo[b]thienyl, 5-benzo[b]thienyl, 2-benzo[b]-thienyl, 4-dibenzofuryl, 4,7-dibenzofuryl, 4-methyl-7-dibenzofuryl, 2-xanthenyl, 8-methyl-2-xanthenyl, 3-xanthenyl, 2-phenoxathlinyl, 2,7-phenoxathlinyl, 2-pyrrolyl, 3-pyrrolyle, 5-methyl-3-pyrrolyl, 2-imidazolyl, 4-imidazolyl, 5-imidazolyl, 2-methyl-4-imidazolyl, 2-ethyl-4-imidazolyl, 2-ethyl-5-imidazolyl, 3-pyrazolyl, 1-methyl-3-pyrazolyl, 1-propyl-4-pyrazolyl, 2-pyrazinyl, 5,6-dimethyl-2-pyrazinyl, 2-indolizinyl, 2-methyl-3-isoindolyl, 2-methyl-1-isoindolyl, 1-methyl-2-indolyl, 1-methyl-3-indolyl, 1,5-dimethyl-2-indolyl, 1-methyl-3-indazolyl, 2,7-dimethyl-8-purinyl, 2-methoxy-7-methyl-8-purinyl, 2-quinolizinyl, 3-isoquinolyl, 6-isoquinolyl, 7-isoquinolyl, isoquinolyl, 3-methoxy-6-isoquinolyl, 2-quinolyl, 6-quinolyl, 7-quinolyl, 2-methoxy-3-quinolyl, 2-methoxy-6-quinolyl, 6-phthalazinyl, 7-phthalazinyl, 1-methoxy-6-phthalazinyl, 1,4-dimethoxy-6-phthalazinyl, 1,8-naphthyridin-2-yl, 2-quinoxalinyl, 6-quinoxalinyl, 2,3-dimethyl-6-quinoxalinyl, 2,3-dimethoxy-6-quinoxalinyl, 2-quinazolinyl, 7-quinazolinyl, 2-dimethylamino-6-quinazolinyl, 3-cinnolinyl, 6-cinnolinyl, 7-cinnolinyl, 3-methoxy-7-cinnolinyl, 2-pteridinyl, 6-pteridinyl, 7-pteridinyl, 6,7-dimethoxy-2-pteridinyl, 2-carbazolyl, 3-carbazolyl, 9-methyl-2-carbazolyl, 9-methyl-3-carbazolyl, β-carbolin-3-yl, 1-methyl-β-carbolin-3-yl, 1-methyl-β-carbolin-6-yl, 3-phenanthridinyl, 2-acridinyl, 3-acridinyl, 2-perimidinyl, 1-methyl-5-perimidinyl, 5-phenanthrolinyl, 6-phenanthrolinyl, 1-phenazinyl, 2-phenazinyl, 3-isothiazolyl, 4-isothiazolyl, 5-isothiazolyl, 2-phenothiazinyl, 3-phenothiazinyl, 10-methyl-3-phenothiazinyl, 3-isoxazolyl, 4-isoxazolyl, 5-isoxazolyl, 4-methyl-3-furazanyl, 2-phenoxazinyl or 10-methyl-2-phenoxazinyl.

Particularly preferred above substituents are naphthyl, phenanthryl, anthryl, 5,6,7,8-tetrahydro-2-naphthyl, 5,6,7,8-tetrahydro-1-naphthyl, thienyl, benzo[b]thienyl, naphtho[2, 3-b]-thienyl, thiathrenyl, dibenzofuryl, chromenyl, xanthenyl, phenoxathlinyl, pyrrolyl, isoindolyl, indolyl, phenothiazinyl, biphenyl, terphenyl, fluorenyl or phenoxazinyl, each unsubstituted or substituted by $C_1$–$C_4$alkyl, $C_1$–$C_4$alkoxy, $C_1$–$C_4$alkylthio, hydroxy, phenylamino or di($C_1$–$C_4$alkyl)amino, typically 1-naphthyl, 2-naphthyl, 1-phenylamino-4-naphthyl, 1-methylnaphthyl, 2-methylnaphthyl, 1-methoxy-2-naphthyl, 2-methoxy-1-naphthyl, 1-dimethylamino-2-naphthyl, 1,2-dimethyl-4-naphthyl, 1,2-dimethyl-6-naphthyl, 1,2-dimethyl-7- naphthyl, 1,3-dimethyl-6-naphthyl, 1,4-dimethyl-6-naphthyl, 1,5-dimethyl-2-naphthyl, 1,6-dimethyl-2-naphthyl, 1-hydroxy-2-naphthyl, 2-hydroxy-1-naphthyl, 1,4-dihydroxy-2-naphthyl, 7-phenanthryl, 1-anthryl, 2-anthryl, 9-anthryl, 3-benzo[b]thienyl, 5-benzo[b]thienyl, 2-benzo[b]thienyl, 4-dibenzofuryl, 4,7-dibenzofuryl, 4-methyl-7-dibenzofuryl, 2-xanthenyl, 8-methyl-2-xanthenyl, 3-xanthenyl, 2-pyrrolyl, 3-pyrrolyl, 2-phenothiazinyl, 3-phenothiazinyl, 10-methyl-3-phenothiazinyl.

Halogen substituents will conveniently be chloro, bromo or iodo. Chloro is preferred.

Alkanoyl of up to 25 carbon atoms inclusive is a branched or unbranched radical, typically including formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl. Alkanoyl of 2 to 18, most preferably 2 to 12, e.g. 2 to 6, carbon atoms, is preferred. Acetyl is particularly preferred.

$C_2$–$C_{25}$Alkanoyl substituted by a di($C_1$–$C_6$alkyl) phosphonate group will typically be $(CH_3CH_2O)_2$ $POCH_2CO-$, $(CH_3O)_2POCH_2CO-$, $(CH_3CH_2CH_2CH_2O)_2$ $POCH_2CO-$, $(CH_3CH_2O)_2$ $POCH_2CH_2CO-$, $(CH_3O)_2$ $POCH_2CH_2CO-$, $(CH_3CH_2CH_2CH_2O)_2$ $POCH_2CH_2CO-$, $(CH_3CH_2O)_2PO(CH_2)_4CO-$, $(CH_3CH_2O)_2PO(CH_2)_8CO-$ or $(CH_3CH_2O)_2$ $PO(CH_2)_{17}CO-$.

Alkanoyloxy of up to 25 carbon atoms is an unbranched or branched radical and is typically formyloxy, acetoxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, eicosanoyloxy or docosanoyloxy. Alkanoyloxy of 2 to 18, preferably 2 to 12, e.g. 2 to 6, carbon atoms is preferred. Acetoxy is particularly preferred.

Alkenoyl of 3 to 25 carbon atoms is a branched or unbranched radical, typically including propenoyl, 2-butenoyl, 3-butenoyl, isobutenoyl, n-2,4-pentadienoyl, 3-methyl-2-butenoyl, n-2-octenoyl, n-2-dodecenoyl, isododecenoyl, oleoyl, n-2-octadecenoyl or n-4-octadecenoyl. Alkenoyl of 3 to 18, preferably 3 to 12, e.g. 3 to 6, most preferably 3 to 4, carbon atoms is preferred.

$C_3$–$C_{25}$Alkenoyl interrupted by oxygen, sulfur or

is typically $CH_3OCH_2CH_2CH=CHCO-$ or $CH_3OCH_2CH_2OCH=CHCO-$.

Alkenoyloxy of 3 to 25 carbon atoms is a branched or unbranched radical, typically including propenoyloxy, 2-butenoyloxy, 3-butenoyloxy, isobutenoyloxy, n-2,4-pentadienoyloxy, 3-methyl-2-butenoyloxy, n-2-octenoyloxy, n-2-dodecenoyloxy, isododecenoyloxy, oleoyloxy, n-2-octadecenoyloxy or n-4-octadecenoyloxy. Alkenoyloxy of 3 to 18, preferably 3 to 12, typically 3 to 6, most preferably 3 to 4, carbon atoms is preferred.

$C_3$–$C_{25}$Alkenoyloxy interrupted by oxygen, sulfur or

will typically be $CH_3OCH_2CH_2CH=CHCOO-$ or $CH_3OCH_2CH_2OCH=CHCOO-$.

$C_3$–$C_{25}$-Alkanoyl interrupted by oxygen, sulfur or

will typically be $CH_3-O-CH_2CO-$, $CH_3-S-CH_2CO-$, $CH_3-NH-CH_2CO-$, $CH_3-N(CH_3)-CH_2CO-$, $CH_3-O-CH_2CH_2-O-CH_2CO-$, $CH_3-(O-CH_2CH_2-)_2O-CH_2CO-$, $CH_3-(O-CH_2CH_2-)_3O-CH_2CO-$ or $CH_3-(O-CH_2CH_2-)_4O-CH_2CO-$.

$C_3$–$C_{25}$-Alkanoyloxy interrupted by oxygen, sulfur or

will typically be $CH_3-O-CH_2COO-$, $CH_3-S-CH_2COO-$, $CH_3-NH-CH_2COO-$, $CH_3-N(CH_3)-CH_2COO-$, $CH_3-O-CH_2CH_2-O-CH_2COO-$, $CH_3-(O-CH_2CH_2-)_2O-CH_2COO-$, $CH_3-(O-CH_2CH_2-)_3O-CH_2COO-$ or $CH_3-(O-CH_2CH_2-)_4O-CH_2COO-$.

$C_6$–$C_9$Cycloalkylcarbonyl is typically cyclopentylcarbonyl, cyclohexylcarbonyl, cycloheptylcarbonyl or cyclooctylcarbonyl. Cyclohexylcarbonyl is preferred.

$C_6$–$C_9$Cycloalkylcarbonyloxy is typically cyclopentylcarbonyloxy, cyclohexylcarbonyloxy, cycloheptylcarbonyloxy or cyclooctylcarbonyloxy. Cyclohexylcarbonyloxy is preferred.

$C_1$–$C_{12}$Alkyl-substituted benzoyl which preferably carries 1 to 3, most preferably 1 or 2, alkyl groups, is typically o-, m- or p-methylbenzoyl, 2,3-dimethylbenzoyl, 2,4-dimethylbenzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4-tert-butylbenzoyl, 2-ethylbenzoyl, 2,4,6-trimethylbenzoyl, 2,6-dimethyl-4-tert-butylbenzoyl or 3,5-di-tert-butylbenzoyl. Preferred substituents are $C_1$–$C_8$alkyl, most preferably $C_1$–$C_4$alkyl.

$C_1$–$C_{12}$Alkyl-substituted benzoyloxy which preferably carries 1 to 3, most preferably 1 or 2, alkyl groups, is typically o-, m- or p-methylbenzoyloxy, 2,3-dimethylbenzoyloxy, 2,4-dimethylbenzoyloxy, 2,5-dimethylbenzoyloxy, 2,6-dimethylbenzoyloxy, 3,4-dimethylbenzoyloxy, 3,5-dimethylbenzoyloxy, 2-methyl-6-ethylbenzoyloxy, 4-tert-butylbenzoyloxy, 2-ethylbenzoyloxy, 2,4,6-trimethylbenzoyloxy, 2,6-dimethyl-4-tert-butylbenzoyloxy or 3,5-di-tert-butylbenzoyloxy. Preferred substituents are $C_1$–$C_8$alkyl, preferably $C_1$–$C_4$alkyl.

Alkyl of up to 25 carbon atoms is a branched or unbranched radical and is typically methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. A preferred meaning of $R_2$ and $R_4$ is typically $C_1$–$C_{18}$alkyl. A particularly preferred meaning of $R_4$ is $C_1$–$C_4$alkyl.

Alkenyl of 3 to 25 carbon atoms is a branched or unbranched radical, typically including propenyl, 2-butenyl, 3-butenyl, isobutenyl, n-2,4-pentadienyl, 3-methyl-2-butenyl, n-2-octenyl, n-2-dodecenyl, isododecenyl, oleyl, n-2-octadecenyl or n-4-octadecenyl. Alkenyl of 3 to 18, preferably 3 to 12, typically 3 to 6, most preferably 3 to 4, carbon atoms is preferred.

Alkenyloxy of 3 to 25 carbon atoms is a branched or unbranched radical, typically including propenyloxy, 2-butenyloxy, 3-butenyloxy, isobutenyloxy, n-2,4-pentadienyloxy, 3-methyl- 2-butenyloxy, n-2-octenyloxy, n-2-dodecenyloxy, isododecenyloxy, oleyloxy, n-2-octadecenyloxy or n-4-octadecenyloxy. Alkenyloxy of 3 to 18, preferably 3 to 12, typically 3 to 6, most preferably 3 to 4, carbon atoms is preferred.

Alkynyl of 3 to 25 carbon atoms is a branched or unbranched radical, typically including propynyl (—$CH_2$—C≡CH), 2-butynyl, 3-butynyl, n-2-octynyl or n-2-dodecynyl. Alkynyl of 3 to 18, preferably 3 to 12, typically 3 to 6, most preferably 3 to 4, carbon atoms is preferred.

Alkynyloxy of 3 to 25 carbon atoms is a branched or unbranched radical, typically including propynyloxy (—$OCH_2$—C≡CH), 2-butynyloxy, 3-butynyloxy, n-2-octynyloxy, or n-2-dodecynyloxy. Alkynyloxy of 3 to 18, preferably 3 to 12, typically 3 to 6, most preferably 3 to 4, carbon atoms is preferred.

$C_2$–$C_{25}$Alkyl interrupted by oxygen, sulfur or

will typically be $CH_3$—O—$CH_2$—, $CH_3$—S—$CH_2$—, $CH_3$—NH—$CH_2$—, $CH_3$—N($CH_3$)—$CH_2$—, $CH_3$—O—$CH_2CH_2$—O—$CH_2$—, $CH_3$—(O—$CH_2CH_2$—)$_2$O—$CH_2$—, $CH_3$—(O—$CH_2CH_2$—)$_3$O—$CH_2$— or $CH_3$-(O-$CH_2CH_2$—)$_4$O—$CH_2$—.

$C_7$–$C_9$Phenylalkyl may typically be benzyl, α-methylbenzyl, α,α-dimethylbenzyl or 2-phenylethyl. Benzyl and α,α-dimethylbenzyl are preferred.

$C_7$–$C_9$-Phenylalkyl which is unsubstituted or substituted in the phenyl moiety by 1 to 3 $C_1$–$C_4$alkyl groups will typically be benzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tert-butylbenzyl. Benzyl is preferred.

$C_7$–$C_{25}$Phenylalkyl which is interrupted by oxygen, sulfur or

and is unsubstituted or substituted in the phenyl moiety by 1 to 3 $C_1$–$C_4$alkyl groups is a branched or unbranched radical such as phenoxymethyl, 2-methylphenoxymethyl, 3-methylphenoxymethyl, 4-methylphenoxymethyl, 2,4-dimethylphenoxymethyl, 2,3-dimethylphenoxymethyl, phenylthiomethyl, N-methyl-N-phenyl-methyl, N-ethyl-N-phenylmethyl, 4-tert-butylphenoxymethyl, 4-tert-butylphenoxyethoxymethyl, 2,4-di-tert-butylphenoxymethyl, 2,4-di-tert-butylphenoxyethoxymethyl, phenoxyethoxyethoxyethoxymethyl, benzyloxymethyl, benzyloxyethoxymethyl, N-benzyl-N-ethylmethyl or N-benzyl-N-isopropylmethyl.

$C_7$–$C_9$Phenylalkoxy is typically benzyloxy, α-methylbenzyloxy, α,α-dimethylbenzyloxy or 2-phenylethoxy. Benzyloxy is preferred.

$C_1$–$C_4$Alkyl-substituted phenyl that preferably contains 1 to 3, preferably 1 or 2, alkyl groups, will typically be o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

$C_1$–$C_4$Alkyl-substituted phenoxy which preferably contains 1 to 3, most preferably 1 or 2, alkyl groups, is typically o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

Unsubstituted or $C_1$–$C_4$alkyl-substituted $C_5$–$C_8$cycloalkyl is typically cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Cyclohexyl and tertbutylcyclohexyl are preferred.

Unsubstituted or $C_1$–$C_4$alkyl-substituted $C_5$–$C_8$cycloalkoxy is typically cyclopentoxy, methylcyclopentoxy, dimethylcyclopentoxy, cyclohexoxy, methylcyclohexoxy, dimethylcyclohexoxy, trimethylcyclohexoxy, tert-butylcyclohexoxy, cycloheptoxy or cyclooctoxy. Cyclohexoxy and tert-butylcyclohexoxy are preferred.

Alkoxy of up to 25 carbon atoms is a branched or unbranched radical and is typically methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. Alkoxy of 1 to 12, preferably 1 to 8, e.g. 1 to 6, carbon atoms is preferred.

$C_2$–$C_{25}$Alkoxy interrupted by oxygen, sulfur or

is typically $CH_3$—O—$CH_2O$—, $CH_3$—S—$CH_2CH_2O$—, $CH_3$—NH—$CH_2CH_2O$—, $CH_3$—N($CH_3$)—$CH_2CH_2O$—, $CH_3$—O—$CH_2CH_2$—O—$CH_2CH_2O$—, $CH_3$—(O—$CH_2CH_2$—)$_2$O—$CH_2CH_2O$—, $CH_3$—(O—$CH_2CH_2$—)$_3$O—$CH_2CH_2O$— or $CH_3$—(O—$CH_2CH_2$—)$_4$O—$CH_2CH_2O$—.

Alkylthio of up to 25 carbon atoms is a branched or unbranched radical and is typically methylthio, ethylthio, propylthio, isopropylthio, n-butylthio, isobutylthio, pentylthio, isopentylthio, hexylthio, heptylthio, octylthio, decylthio, tetradecylthio, hexadecylthio or octadecylthio. Alkylthio of 1 to 12, preferably 1 to 8, e.g. 1 to 6, carbon atoms is preferred.

Alkylamino of up to 4 carbon atoms is a branched or unbranched radical and is typically methylamino, ethylamino, propylamino, isopropylamino, n-butylamino, isobutylamino or tert-butylamino.

Di(C₁–C₄)alkylamino also signifies that the two moieties, each independently of the other, are branched or unbranched, and is typically dimethylamino, methylethylamino, diethylamino, methyl-n-propylamino, methylisopropylamino, methyl-n-butylamino, methylisobutylamino, ethylisopropylamino, ethyl-n-butylamino, ethylisobutylamino, ethyl-tert-butylamino, diethylaamino, diisopropylamino, isopropyl-n-butylamino, isopropylisobutylamino, di-n-butylamino or diisobutylamino.

Alkanoylamino of up to 25 carbon atoms is an unbranched or branched radical and is typically formylamino, acetylamino, propionylamino, butanoylamino, pentanoylamino, hexanoylamino, heptanoylamino, octanoylamino, nonanoylamino, decanoylamino, undecanoylamino, dodecanoylamino, tridecanoylamino, tetradecanoylamino, pentadecanoylamino, hexadecanoylamino, heptadecanoylamino, octadecanoylamino, eicosanoylamino oder docosanoylamino. Alkanoylamino of 2 to 18, preferably 2 to 12, e.g. 2 to 6, carbon atoms is preferred.

$C_1$–$C_{18}$Alkylene is a branched or unbranched radical, typically methylene, ethylene, propylene, trimethylene, tetramethylene, pentamethylene, hexamethylene, heptamethylene, octamethylene, decamethylene, dodecamethylene or octadecamethylene. $C_1$–$C_{12}$Alkylene is preferred, and $C_1$–$C_8$alkylene is particularly preferred.

A $C_1$–$C_4$alkyl-substituted $C_5$–$C_{12}$cycloalkylene ring which preferably contains 1 to 3, preferably 1 or 2 branched or unbranched alkyl groups will typically be cyclopentylene, methylcyclopentylene, dimethylcyclopentylene, cyclohexylene, methylcyclohexylene, dimethylcyclohexylene, trimethylcyclohexylene, tert-butylcyclohexylene, cycloheptylene, cyclooctylene or cyclodecylene. Cyclohexylene and tert-butylcyclohexylene.

$C_2$–$C_{18}$Alkylene which is interrupted by oxygen, sulfur or

will typically be —CH₂—O—CH₂—, —CH₂—S—CH₂—, —CH₂—NH—CH₂—, —CH₂—N(CH₃)—CH₂—, —CH₂—O—CH₂CH₂—O—CH₂—, —CH₂—(O—CH₂CH₂—)₂O—CH₂—, —CH₂—(O—CH₂CH₂—)₃O—CH₂—, —CH₂—(O—CH₂CH₂—)₄O—CH₂— or —CH₂CH₂—S—CH₂CH₂—.

$C_2$–$C_{18}$Alkenylene is typically vinylene, methylvinylene, octenylethylene or dodecenylethylene. $C_2$–$C_8$Alkenylene is preferred.

Alkylidene of 2 to 20 carbon atoms may typically be ethylidene, propyliden, butylidene, pentylidene, 4-methylpentylidene, heptylidene, nonylidene, tridecylidene, nonadecylidene, 1-methylethylidene, 1-ethylpropylidene or 1-ethylpentylidene. $C_2$–$C_8$Alkylidene is preferred.

Phenylalkylidene of 7 to 20 carbon atoms may typically be benzylidene, 2-phenylethylidene or 1-phenyl-2-hexylidene. $C_7$–$C_9$Phenylalkylidene is preferred.

$C_5$–$C_8$Cycloalkylene is a saturated hydrocarbon group having two free valences and at least one ring unit and is typically cyclopentylene, cyclohexylene, cycloheptylene or cyclooctylene. Cyclohexylene is preferred.

$C_7$–$C_8$Bicycloalkylene may be bicycloheptylene or bicyclooctylene.

Unsubstituted or $C_1$–$C_4$alkyl-substituted phenylene or naphthylene is typically 1,2-, 1,3-, 1,4-phenylene, 1,2-, 1,3-, 1,4-, 1,6-, 1,7-, 2,6- or 2,7-naphthylene. 1,4-phenylene is preferred.

A $C_1$–$C_4$alkyl-substituted $C_5$–$C_8$cycloalkylidene ring that preferably contains 1 to 3, most preferably 1 or 2, branched or unbranched alkyl groups, is typically cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cycloheptylidene or cyclooctylidene. Cyclohexylidene and tert-butylcyclohexylidene are preferred.

A mono-, di- or trivalent metal cation is preferably an alkali metal cation, an alkaline earth metal cation or an aluminium cation, typically Na⁺, K⁺, Mg⁺⁺, Ca⁺⁺ or Al⁺⁺⁺.

Interesting compounds of formula I are those wherein, when n is 1, $R_1$ is phenyl which is unsubstituted or substituted in para-position by $C_1$–$C_{18}$alkylthio or di($C_1$–$C_4$-alkyl)amino; mono- to penta-substituted alkylphenyl containing together a maximum number of 18 carbon atoms in the 1 to 5 alkyl substituents; naphthyl, biphenyl, terphenyl, phenanthryl, anthryl, fluorenyl, carbazolyl, thienyl, pyrrolyl, phenothiazinyl or 5,6,7,8-tetrahydronaphthyl, each unsubstituted or substituted by $C_1$–$C_4$alkyl, $C_1$–$C_4$alkoxy, $C_1$–$C_4$alkylthio, hydroxy or amino.

Preferred compounds of formula I are those wherein, when n is 2, $R_1$ is —$R_{12}$—X—$R_{13}$—, $R_{12}$ and $R_{13}$ are phenylene, X is oxygen or —$NR_{31}$—, and $R_{31}$ is $C_1$–$C_4$alkyl.

Further preferred compounds of formula I are those wherein, when n is 1, $R_1$ is naphthyl, phenanthryl, thienyl, dibenzofuryl, carbazolyl, fluorenyl, each unsubstituted or substituted by $C_1$–$C_4$alkyl, $C_1$–$C_4$alkoxy, $C_1$–$C_4$alkylthio, hydroxy, halogen, amino, $C_1$–$C_4$alkylamino or di($C_1$–$C_4$-alkyl)amino, or is a radical of formula II

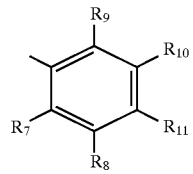

$R_7$, $R_8$, $R_9$ und $R_{10}$ are each independently of one another hydrogen, chloro, bromo, hydroxy, $C_1$–$C_{18}$alkyl, $C_2$–$C_{18}$alkyl which is interrupted by oxygen or sulfur; $C_1$–$C_{18}$-alkoxy, $C_2$–$C_{18}$alkoxy which is interrupted by oxygen or sulfur; $C_1$–$C_{18}$alkylthio, $C_3$–$C_{12}$-alkenyloxy, $C_3$–$C_{12}$alkynyloxy, $C_7$–$C_9$phenylalkyl, $C_7$–$C_9$phenylalkoxy, unsubstituted or $C_1$–$C_4$alkyl-substituted phenyl; phenoxy, cyclohexyl, $C_5$–$C_8$cycloalkoxy; $C_1$–$C_4$alkylamino, di($C_1$–$C_4$alkyl)amino, $C_1$–$C_{12}$alkanoyl, $C_3$–$C_{12}$alkanoyl which is interrupted by oxygen or sulfur; $C_1$–$C_{12}$alkanoyloxy, $C_3$–$C_{12}$alkanoyloxy which is interrupted by oxygen or sulfur; $C_1$–$C_{12}$alkanoylamino, $C_3$–$C_{12}$alkenoyl, $C_3$–$C_{12}$alkenoyloxy, cyclohexylcarbonyl, cyclohexylcarbonyloxy, benzoyl or $C_1$–$C_4$alkyl-substituted benzoyl; benzoyloxy or $C_1$–$C_4$alkyl substituted benzoyloxy;

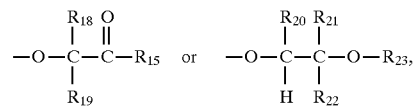

or in formula II each pair of substituents $R_7$ and $R_8$ or $R_8$ and $R_{11}$, together with the linking carbon atoms, forms a benzene ring, $R_{11}$ is hydrogen, $C_1-C_{18}$alkyl, $C_1-C_{18}$alkylthio, $C_7-C_9$phenylalkyl, unsubstituted or $C_1-C_4$-alkyl-substituted phenyl; cyclohexyl, $C_1-C_4$alkylamino, di($C_1-C_4$-alkyl) amino, $C_1-C_{12}$-alkanoyl, $C_3-C_{12}$alkanoyl which is interrupted by oxygen or sulfur; $C_1-C_{12}$alkanoylamino, $C_3-C_{12}$alkenoyl, cyclohexylcarbonyl, benzoyl or $C_1-C_4$alkyl-substituted benzoyl; with the proviso that at least one of $R_7$, $R_8$, $R_9$, $R_{10}$ or $R_{11}$ is not hydrogen;

$R_{15}$ is hydroxy, $C_1-C_{12}$alkoxy or

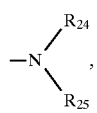

$R_{18}$ and $R_{19}$ are each independently of the other hydrogen or $C_1-C_4$alkyl, $R_{20}$ is hydrogen, $R_{21}$ is hydrogen, phenyl, $C_1-C_{18}$alkyl, $C_2-C_{18}$alkyl which is interrupted by oxygen or sulfur, $C_7-C_9$phenylalkyl, $C_7-C_{18}$phenylalkyl which is interrupted by oxygen or sulfur and which is unsubstituted or substituted in the phenyl moiety by 1 to 3 $C_1-C_4$alkyl groups, and $R_{19}$ and $R_{20}$, together with the linking carbon atoms, form a cyclohexylene ring which is unsubstituted or substituted by 1 to 3 $C_1-C_4$alkyl groups, $R_{22}$ is hydrogen or $C_1-C_4$alkyl, $R_{23}$ is hydrogen, $C_1-C_{18}$alkanoyl, $C_3-C_{12}$alkenoyl, $C_3-C_{12}$alkanoyl which is interrupted by oxygen or sulfur; $C_2-C_{12}$alkanoyl which is substituted by a di($C_1-C_6$alkyl) phosphonate group; $C_6-C_9$cycloalkylcarbonyl, benzoyl,

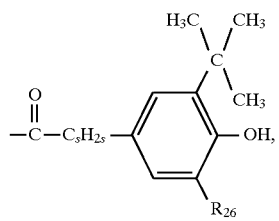

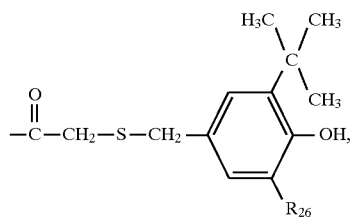

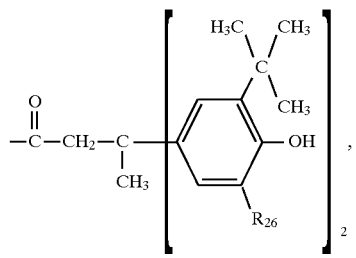

$R_{24}$ and $R_{25}$ are each independently of the other hydrogen or $C_1-C_{12}$alkyl, $R_{26}$ is hydrogen or $C_1-C_4$alkyl, $R_{27}$ is $C_1-C_{12}$alkylene, $C_2-C_8$alkenylene, $C_2-C_8$alkylidene, $C_7-C_{12}$phenylalkylidene, $C_5-C_8$cycloalkylene or phenylene, $R_{28}$ is hydroxy, $C_1-C_{12}$alkoxy or

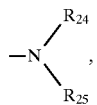

$R_{29}$ is oxygen or —NH—, $R_{30}$ is $C_1-C_{18}$alkyl or phenyl, and s is 1 or 2.

Also preferred are compounds of formula I, wherein, when n is 1, $R_1$ is phenanthryl, thienyl, dibenzofuryl, unsubstituted or $C_1-C_4$alkyl-substituted carbazolyl; or fluorenyl, or $R_1$ is a radical of formula II

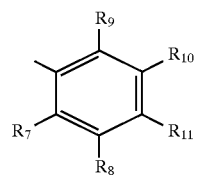

$R_7$, $R_8$, $R_9$ und $R_{10}$ are each independently of one another hydrogen, chloro, hydroxy, $C_1-C_{18}$alkyl, $C_1-C_{18}$alkoxy, $C_1-C_{18}$alkylthio, $C_3-C_4$alkenyloxy, $C_3-C_4$-alkyloxy, phenyl, benzoyl, benzoyloxy or

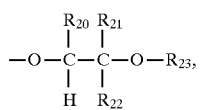

$R_{11}$ is hydrogen, $C_1-C_{18}$alkyl, $C_1-C_{18}$alkylthio, pheny or cyclohexyl; with the proviso that at least one of $R_7$, $R_8$, $R_9$, $R_{10}$ or $R_{11}$ is not hydrogen, $R_{20}$ is hydrogen, $R_{21}$ is hydrogen, phenyl or $C_1-C_{18}$alkyl, or $R_{20}$ and $R_{21}$, together with the linking carbon atoms, form a cyclohexylene ring which is unsubstituted or substituted by 1 to 3 $C_{1-C4}$alkyl groups, $R_{22}$ is hydrogen or $C_1-C_4$alkyl, and $R_{23}$ is hydrogen, $C_1-C_{12}$alkanoyl or benzoyl.

Compounds of formula I are especially preferred, wherein, when n is 1, $R_7$, $R_8$, $R_9$ and $R_{10}$ are each independently of one another hydrogen or $C_1-C_4$alkyl, and $R_{11}$ is hydrogen, $C_1-C_{12}$alkyl, $C_1-C_4$alkylthio or phenyl; with the proviso that at least one of $R_7$, $R_8$, $R_9$, $R_{10}$ or $R_{11}$ is not hydrogen.

Particularly interesting compounds of formula I are those wherein $R_2$, $R_3$, $R_4$ and $R_5$ are each independently of one another hydrogen, chloro, $C_1-C_{18}$alkyl, benzyl, phenyl, $C_5-C_8$cycloalkyl, $C_1-C_{18}$alkoxy, $C_1-C_{18}$alkylthio, $C_1-C_{18}$alkanoyloxy, $C_1-C_{18}$alkanoylamino, $C_3-C_{18}$alkenyloxy or benzoyloxy; with the proviso that, when $R_2$ is hydrogen or methyl, $R_7$ or $R_8$ is not hydroxy or $C_1-C_{25}$alkanoyloxy; or each pair of substituents $R_2$ and $R_3$ or $R_3$ and $R_4$ or $R_4$ and $R_5$, together with the linking carbon atoms, forms a benzene ring, $R_4$ is additionally —$(CH_2)_p$—$COR_{15}$ or —$(CH_2)_q$OH or, if $R_3$, $R_5$ and $R_6$ are hydrogen, $R_4$ is additionally a radical of formula III, $R_{15}$ is hydroxy, $C_1$–$C_{12}$alkoxy or

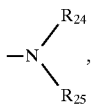

$R_{16}$ and $R_{17}$ are methyl groups or, together with the linking carbon atom, form a $C_5$–$C_8$-cycloalkylidene ring which is unsubstituted or substituted by 1 to 3 $C_1$–$C_4$alkyl groups, $R_{24}$ and $R_{25}$ are each independently of the other hydrogen or $C_1$–$C_{12}$alkyl, p is 1 or 2, and q is 2, 3, 4, 5 or 6.

Particularly interesting compounds of formula I are also those wherein at least two of $R_2$, $R_3$, $R_4$ and $R_5$ are hydrogen.

Compounds of formula I of very particular interest are those wherein $R_3$ and $R_5$ are hydrogen.

Very particularly preferred compounds of formula I are those wherein $R_2$ is $C_1$–$C_4$alkyl, $R_3$ is hydrogen, $R_4$ is $C_1$–$C_4$alkyl or, if $R_6$ is hydrogen, $R_4$ is additionally a radical of formula III, $R_5$ is hydrogen, and $R_{16}$ and $R_{17}$, together with the linking carbon atom, form a cyclohexylidene ring.

The compounds of formula I can be prepared in per se known manner.

Conveniently, a phenol of formula V

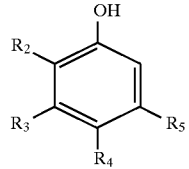

(V)

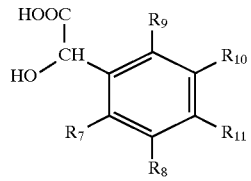

(VI)

wherein $R_2$, $R_3$, $R_4$ and $R_5$ have the given meanings, is reacted with a mandelic acid derivative of formula VI which is substituted at the phenyl ring, wherein $R_7$, $R_8$, $R_9$, $R_{10}$ and $R_{11}$ have the given meanings, at elevated temperature, preferably in the temperature range from 130° to 200° C., in the melt or in a solvent, under normal pressure or a slight vacuum, to the novel compounds of formula I, wherein $R_6$ is hydrogen.

To prepare the novel compounds of formula I, wherein n is 2, $R_6$ is hydrogen and $R_1$ is e.g. —$R_{12}$—X—$R_{13}$—, and $R_{12}$, $R_{13}$ and X have the given meanings, 2 equivalents of the phenol of formula V are used.

It is preferred to carry out the reaction in the presence of a solvent such as acetic acid, propionic acid or formic acid, in the temperature range from 50° to 130° C. The reaction can be catalysed by the addition of an acid such as hydrochloric acid, sulfuric acid or methanesulfonic acid. The reaction may conveniently be carried out as described in the references cited at the outset, in particular according to U.S. Pat. No. 4,325,863, Example 1, column 8, lines 35–45.

The drawback of this process for the preparation of compounds of formula I is that it is necessary to use mandelic acids that are substituted at the phenyl ring or heterocyclic mandelic acids. However, not very many of these acids are known in the literature and the known syntheses for the preparation of these mandelic acids are quite troublesome.

A novel process for the preparation of compounds of formula I, which is also the subject matter of a parallel application, is therefore preferred.

Typically, a compound of formula VII

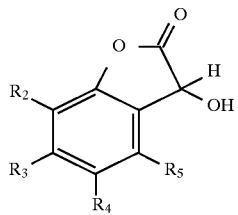

(VII)

[H]$_n$—$R_1$ (VIII)

wherein $R_2$, $R_3$, $R_4$ and $R_5$ have the given meanings, is reacted with a compound of formula VIII, wherein $R_1$ has the given meaning, to compounds of formula I.

The reaction conditions of the inventive process are the following:

The reaction can be carried out at elevated temperature, preferably in the range from 70° to 200° C., in the melt or in a solvent and under normal pressure or slight vacuum.

It is particularly preferred to carry out the reaction in the boiling range of the compound of formula VIII.

The preferred solvent is the compound of formula VIII, which is simultaneously the reactant.

Suitable solvents are those which do not participate in the reaction, typically halogenated hydrocarbons, hydrocarbons, ethers or deactivated aromatic hydrocarbons.

Preferred halogenated hydrocarbons are dichloromethane, 1,2-dichloroethane, chloroform or carbon tetrachloride.

Preferred hydrocarbons are typically octane and the commercially available isomeric fractions such as the hexane faction, white spirit or ligroin.

Preferred ethers are typically dibutyl ether, methyl tert-butyl ether or diethylene glycol dimethyl ether.

Illustrative examples of deactivated aromatic hydrocarbons are nitrobenzene or pyridine.

The water of reaction is preferably removed continuously, preferably by adding an agent that absorbs water, for example a molecular sieve. Most preferably the water is removed continuously as an azeotrope by distillation via a water separator.

This process for the preparation of compounds of formula I is preferably carried out in the presence of a catalyst.

Suitable catalysts are protonic acids, Lewis acids, aluminium silicates, ion exchange resins, zeolites, naturally occurring sheet silicates or modified sheet silicates.

Suitable protonic acids are typically acids of inorganic or organic salts, for example hydrochloric acid, sulfuric acid, phosphoric acid, methanesulfonic acid, p-toluenesulfonic acid or carboxylic acids such as acetic acid. p-Toluenesulfonic acid is particularly preferred.

Illustrative examples of suitable Lewis acids are tin tetrachloride, aluminium chloride, zinc chloride or borotrifluoride etherate. Tin tetrachloride and aluminium chloride are especially preferred.

Illustrative examples of suitable aluminium silicates are those that are widely used in the petrochemical industry and are also known as amorphous aluminium silicates. These compounds contains c. 10–30% of silicon monoxide and 70–90% of aluminium oxide. A particularly preferred aluminium silicate is HA-HPV® available from Ketjen (Akzo).

Illustrative examples of suitable ion exchange resins are styrene-divinylbenzene resins which additionally carry sulfonic acid groups, for example Amberlite 200® and Anberlyst® available from Rohm and Haas, or Dowex 50® available from Dow Chemicals; perfluorinated ion exchange resins such as Nafion H® sold by DuPont; or other superacid ion exchange resins such as those as described by T. Yamaguchi, Applied Catalysis, 61, 1–25 (1990) or M. Hino et al., J. Chem. Soc. Chem. Commun. 1980, 851–852.

Suitable zeolites are typically those widely used in petrochemistry as cracking catalysts and known as crystalline silicon-aluminium oxides of different crystal structure. Particularly preferred zeolites are the Faujasites available from Union Carbide, for example Zeolith X®, Zeolith Y® and ultrastabile Zeolith Y® Zeolith Beta® and Zeolith ZSM-12® available from Mobil Oil Co.; and Zeolith Mordenit® available from Norton.

Suitable naturally occurring sheet silicates are termed "acid clays" and typically include bentonites or montmorillonites, which are degraded, ground, treated with mineral acids and calcined industrially. Particularly suitable naturally occurring sheet silicates are the Fulcat® types available from Laporte Adsorbents Co., for example Fulcat 22A®, Fulcat 22B®, Fulcat 200, Fulcat 300 or Fulcat 400; or the Fulmont® types available from Laporte Adsobents Co., for example Fulmont XMP-30 or Fulmont XMP-40. A particularly preferred catalyst is Fulcat 22B®. The other Fulcat® types and Fulmont® types also belong to this preferred class, because there are only minor differences between the individual types, as for example in the number of acid centres.

Modified sheet silicates are also termed "pillared clays" and are derived from the above described naturally occurring sheet silicates by additionally containing between the silicate layers oxides of e.g. zirconium, iron, zinc, nickel, chromium, cobalt or magnesium. This type of catalyst is widely used, as described in the literature, inter alia by J. Clark et al., J. Chem. Soc. Chem. Commun. 1989, 1353–1354, but is available from only a very few firms. Particularly preferred modified sheet silicates typically include Envirocat EPZ-10®, Envirocat EPZG® or Envirocat EPIC® available from Contract Chemicals.

Preferred catalysts are naturally occurring sheet silicates or modified sheet silicates.

Especially preferred is the process for the preparation of compounds of formula I, wherein the reaction is carried out in the presence of a catalyst of the Fulcat® type.

The catalyst is conveniently added in an amount of 1 to 60% by weight and, if a particularly preferred catalyst of the Fulcat® type is used, in an amount of 1 to 30% by weight, with respect to the compound of formula VII.

A particularly interesting process is also that for the preparation of compounds of formula I, wherein, when n is 1, the molar ratio of the compound of formula VII to the compound of formula VIII is 1:1 to 1:20, and, when n is 2, the molar ratio of the compound of formula VII to the compound of formula VIII is 3:1 to 2:1.

Before the reaction with a compound of formula VIII, the compounds of formula VII can be subjected to an additional reaction step by substituting the hydroxyl group in the compound of formula VII by halogen or activating said hydroxyl group with a leaving group. The reaction to give the compounds of formula IX

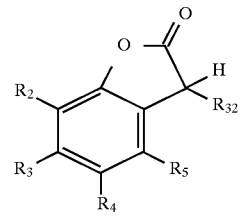

(IX)

wherein $R_{32}$ is halogen or $-OR'_{32}$, and $R'_{32}$ is typically $C_1-C_{25}$alkanoyl, $C_3-C_{25}$alkenoyl, $C_3-C_{25}$alkanoyl which is interrupted by oxygen, sulfur or

$C_6-C_9$cycloalkylcarbonyl, thenoyl, furoyl, benzoyl or $C_1-C_{12}$alkyl-substituted benzoyl; naphthoyl or $C_1-C_{12}$-alkyl-substituted naphthoyl; $C_1-C_{25}$alkanesulfonyl, fluoro-substituted $C_1-C_{25}$-alkanesulfonyl; phenylsulfonyl or $C_1-C_{12}$alkyl-substituted phenylsulfonyl, can be carried out in accordance with known substitution reactions described, inter alia, in Organikum 1986, pages 186–191; or by esterification reactions described, inter alia, in Organikum 1986, pages 402–408.

Halogen substituents will conveniently be chloro, bromo or iodo. Chloro is preferred.

Alkanoyl of up to 25 carbon atoms inclusive is a branched or unbranched radical, typically including formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl. $R'_{32}$ defined as alkanoyl preferably contains 2 to 18, most preferably 2 to 12, e.g. 2 to 6, carbon atoms. Acetyl is particularly preferred.

Alkenoyl of 3 to 25 carbon atoms is a branched or unbranched radical, typically including propenoyl, 2-butenoyl, 3-butenoyl, isobutenoyl, n-2,4-pentadienoyl, 3-methyl-2-butenoyl, n-2-octenoyl, n-2-dodecenoyl, isododecenoyl, oleoyl, n-2-octadecenoyl or n-4-octadecenoyl. Alkenoyl of 3 to 18, preferably 3 to 12, e.g. 3 to 6, most preferably 3 to 4, carbon atoms is preferred.

$C_3-C_{25}$-Alkanoyl interrupted by oxygen, sulfur or

will typically be $CH_3-O-CH_2CO-$, $CH_3-S-CH_2CO-$, $CH_3-NH-CH_2CO-$, $CH_3-N(CH_3)-CH_2CO-$, $CH_3-O-CH_2CH_2-O-CH_2CO-$, $CH_3-(O-CH_2CH_2-)_2O-CH_2CO-$, $CH_3-(O-CH_2CH_2-)_3O-CH_2CO-$ or $CH_3-(O-CH_2CH_2-)_4O-CH_2CO-$.

$C_6-C_9$Cycloalkylcarbonyl is typically cyclopentylcarbonyl, cyclohexylcarbonyl, cycloheptylcarbonyl or cyclooctylcarbonyl. Cyclohexylcarbonyl is preferred.

$C_1-C_{12}$Alkyl-substituted benzoyl which preferably carries 1 to 3, most preferably 1 or 2 alkyl groups, is typically o-, m- or p-methylbenzoyl, 2,3-dimethylbenzoyl, 2,4-dimethylbenzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4-tert-butylbenzoyl, 2-ethylbenzoyl, 2,4,6-trimethylbenzoyl, 2,6- dimethyl-4-tert-butylbenzoyl or 3,5-di-tert-butylbenzoyl. Preferred substituents are $C_1$–$C_9$alkyl, most preferably $C_1$–$C_4$alkyl.

$C_1$–$C_{12}$Alkyl-substituted naphthoyl, which is 1-naphthoyl or 2-naphthoyl and preferably contains 1 to 3, most preferably 1 or 2 alkyl groups, will typically be 1-, 2-, 3-, 4-, 5-, 6-, 7- or 8-methylnaphthoyl, 1-, 2-, 3-, 4-, 5-, 6-, 7- or 8-ethylnaphthoyl, 4-tert-butylnaphthoyl or 6-tert-butylnaphthoyl. Particularly preferred substituents are $C_1$–$C_9$alkyl, most preferably $C_1$–$C_4$alkyl.

$C_1$–$C_{25}$Alkanesulfonyl is a branched or unbranched radical, typically methanesulfonyl, ethanesulfonyl, propanesulfonyl, butanesulfonyl, pentanesulfonyl, hexanesulfonyl, heptanesulfonyl, octanesulfonyl, nonanesulfonyl or docosanesulfonyl. Alkanesulfonyl of 1 to 18, preferably 1 to 12, e.g. 2 to 6, carbon atoms is preferred. Methanesulfonyl is particularly preferred.

Fluoro-substituted $C_1$–$C_{25}$alkanesulfonyl is typically trifluoromethanesulfonyl.

$C_1$–$C_{12}$Alkyl-substituted phenylsulfonyl which carries preferably 1 to 3, most preferably 1 or 2, alkyl groups is typically o-, m- or p-methylphenylsulfonyl, p-ethylphenylsulfonyl, p-propylphenylsulfonyl or p-butylphenylsulfonyl. Preferred substituents are $C_1$–$C_8$alkyl, most preferably $C_1$–$C_4$alkyl. p-Methylphenylsulfonyl is particularly preferred.

Thus, for example, the reaction of compounds of formula VII with a hydrohalic acid, a halide of an oxysulfuric acid, a halide of phosphoric acid, a halide of a phosphorous acid, an acid of formula X

$$R'_{32}\text{—OH} \qquad (X)$$

an acid halide of formula XI,

$$R'_{32}\text{—Y} \qquad (XI)$$

an ester of formula XII

$$R'_{32}\text{—O—}R_{33} \qquad (XII)$$

a symmetrical or unsymmetrical anhydride of formula XIII

$$R'_{32}\text{—O—}R'_{32} \qquad (XIII)$$

or an isocyanate of formula XIV

$$R_{34}\text{—N=C=O} \qquad (XIV)$$

wherein $R'_{32}$ in formula XIII may be different or identical,
Y is fluoro, chloro, bromo or iodo,
$R_{33}$ is $C_1$–$C_8$alkyl, and
$R_{34}$ is $C_1$–$C_{25}$alkyl, unsubstituted or $C_1$–$C_4$alkyl-substituted phenyl, gives the compounds of formula IX in good yield.

Suitable hydrohalic acids are typically hydrochloric acid, hydrobromic acid or hydriodic acid. Hydrochloric acid is preferred.

Suitable halides of an oxysulfuric acid are typically thionyl chloride, sulfuryl chloride or thionyl bromide. Thionyl chloride is preferred.

Suitable halides of phosphoric acid and phosphorous acid typically include phosphorus trichloride, phosphorus tribromide, phosphorus triiodide, phosphorus pentachloride, phosphoroxy chloride or phosphorus pentafluoride. Phosphoroxy chloride is particularly preferred.

A preferred meaning of Y is chloro.

Preferred leaving groups are typically carboxylates such as acetates; alkanesulfonates such as mesylates; or arylsulfonates such as tosylates.

In this reaction step it is preferred to use a halide of an oxysulfuric acid such as thionyl chloride; an acid halide of formula XI; an ester of formula XII; or a symmetrical anhydride of formula XIII.

When using a halide of an oxysulfuric acid such as thionyl chloride, it is preferred to carry out the reaction of a compound of formula VII without a solvent and in the temperature range from 0° to 40° C., preferably at room temperature. The thionyl chloride is conveniently used in a 2- to 10-fold excess, preferably in a 2- to 6-fold excess, with respect to the compound of formula VII. The reaction can also be carried out in the presence of a catalyst such as dimethyl formamide.

When using an acid of formula X ($R'_{32}$—OH), the reaction is preferably carried out with a compound of formula VII in the presence of an inert organic solvent such as dichloromethane, dioxane, diethyl ether or tetrahydrofuran, and in the presence of a reagent that bonds water physically or chemically, conveniently a molecular sieve or dicyclohexylcarbodiimide.

If an acid halide of formula XI ($R'_{32}$—Y), wherein Y is preferably chloro or bromo, most preferably chloro, is used in process step b), it is preferred to carry out the reaction of the compound of formula VII in the presence of a solvent and a base.

The base can be used in varying amounts, from catalytic through stochiometric amounts to the multiple molar excess with respect to the compound of formula VII. The hydrogen chloride formed during the reaction may be converted by the base into the chloride, which can be removed by filtration and/or washing with a suitable aqueous or solid phase, in which case a second water-immiscible solvent can also be used. The product is conveniently purified by recrystallising the residue of the organic phase, which is concentrated or evaporated to dryness.

Suitable solvents for carrying out the reaction include hydrocarbons (typically toluene, xylene, hexane, pentane or further petroleum ether fractions), halogenated hydrocarbons (typically di- or trichloromethane, 1,2-dichloroethan, 1,1,1,-trichloroethane), ethers (e.g. diethyl ether, dibutyl ether or tetrahydrofuran), and also acetonitrile, dimethyl formamide, dimethyl sulfoxide, N-methylpyrrolidone.

Suitable bases include tertiary amines, e.g. trimethylamine, triethylamine, tributylamine, N,N-dimethylaniline, N,N-diethylaniline; pyridines; hydrides (e.g. lithium, sodium or potassium hydride) or alcoholates (e.g. sodium methylate).

If an ester of formula XII ($R'_{32}$—O—$R_{33}$), wherein $R_{33}$ is preferably $C_1$–$C_4$alkyl, most preferably methyl or ethyl, is used in process step b), it is preferred to carry out the reaction of the compound of formula VII in the presence of a solvent that forms an azeotropic mixture with alcohols. The alcohol ($R_{33}$—OH) that forms during the reaction can be removed continuously by distillation.

Suitable solvents that form an azeotropic mixture with alcohols do not participate in the reaction and typically include hydrocarbons such as cyclohexane; aromatic hydrocarbons such as benzene or toluene; halogenated hydrocarbons such as 1,2-dichloroethane; or ethers such as methyl tert-butyl ether.

The reaction can be catalysed with a minor amount of a protonic acid such as p-toluenesulfonic acid, methanesulfonic acid, sulfuric acid or hydrochloric acid; as well as of a Lewis acid such as borotrifluoride etherate or aluminium chloride.

If a symmetrical anhydride of formula XIII ($R'_{32}$—O—$R'_{32}$), wherein $R'_{32}$ is preferably $C_2$-$C_6$alkanoyl, preferably acetyl, is used in process step b), it is preferred to carry out the reaction with a compound of formula VII without the addition of a further solvent and in the temperature range from 20° to 200° C., e.g. the boiling temperature of the anhydride of formula XIII, preferably from 60° to 180° C.

If an isocyanate of formula XIV ($R_{34}$—N=C=O) is used, it is preferred to carry out the reaction with a compound of formula VII without the addition of a further solvent and in the temperature range from 20° to 200° C., e.g. the boiling temperature of the isocyanate of formula XIV, preferably from 60° to 180° C.

The reaction with an isocyanate is likewise preferably carried out in the presence of a catalyst. Preferred catalysts correspond to those referred to above previously in connection with the reaction of the alcohol of formula VII with the compound of formula VIII above.

In the process of this invention for the preparation of the novel compounds of formula I, wherein $R_6$ is hydrogen, the compounds of formula VIII, which also yield mixtures of isomers in other known electrophilic substitution reactions, likewise give compounds of formula I in the form of mixtures of isomers. The relative distribution of the isomers will depend on the commonly known basic rules of organic chemistry for electrophilic aromatic substitution reactions.

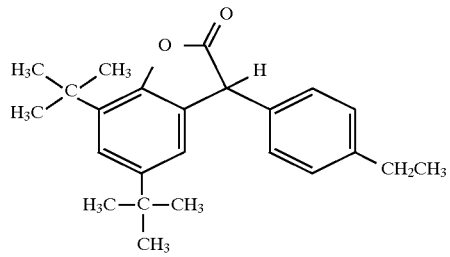
(105)

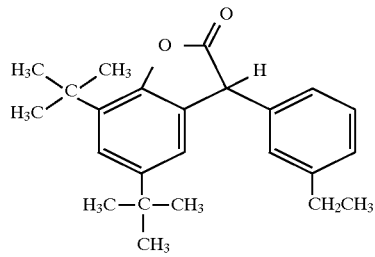
(105A)

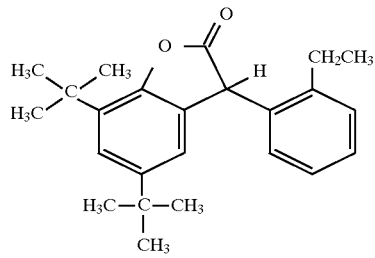
(105B)

As described in Example 4, reaction of e.g. 5,7-di-tert-butyl-3-hydroxy-3H-benzofuran-2-one (compound (201), Table 2) with ethyl benzene, using Fulcat 22B as catalyst, gives 59.2% of the para-isomer (compound (105), Table 1), 10.8% of the meta-isomer (compound (105A) and 21.1% of the ortho-isomer (compound (105B).

The isomers can be purified and separated by fractional crystallisation or chromatography on e.g. silica gel. It is preferred to use the mixtures of isomers as stabilisers for organic materials.

The compounds of formula I can be obtained in different crystal modifications.

The compounds of formula VIII are novel and some are commercially available or can be prepared by per se known methods.

Some of the compounds of formula VII are known in the literature, and have been mentioned, inter alia, in Beilstein 18, 17 and Beilstein E III/IV, 18, 154–166, or described by Th. Kappe et al., Monatshefte für Chemie 99, 990 (1968); J. Morvan et al., Bull. Soc. Chim. Fr. 1979, 583; L. F. Clarke et al., J. Org. Chem. 57, 362 (1992); M. Julia et al., Bull. Soc. Chim. Fr. 1965, 2175, or by H. Sterk et al., Monatshefte für Chemie 99, 2223 (1968). Novel compounds of formula VII can be prepared by methods analogous to those described in these references.

Preferred, however, is a novel process for the preparation of compounds of formula VII

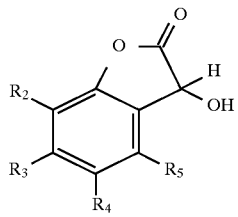
(VII)

which process is the subject matter of a parallel patent application, wherein the general symbols are as defined for formula I, which comprises reacting 1 equivalent of the phenol of formula V

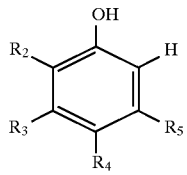
(V)

wherein the general symbols are as defined in connection with the novel compounds of formula I, with 0.8 to 2.0 equivalents, preferably 0.8 to 1.2 equivalents, of glyoxylic acid.

The glyoxylic acid can be used either in crystalline form or, conveniently, in the form of a commercial aqueous solution, usually a 40 to 60% aqueous solution.

The water present in the glyoxylic acid and the water of reaction is removed by distillation during the reaction, conveniently using a solvent that forms an azeotropic mixture with water.

Suitable solvents that form an azeotropic mixture with water do not participate in the reaction and typically include hydrocarbons such as cyclohexane; aromatic hydrocarbons such as benzene or toluene; halogenated hydrocarbons such as 1,2-dichloroethane; or ethers such as methyl tert-butyl ether.

When carrying out the reaction of the phenol of formula V with glyoxylic acid without a solvent to give the compounds of formula VII in the melt, the water of reaction is conveniently distilled off under normal pressure, preferably under a slight vacuum.

It is preferred to carry out the reaction at elevated temperature, preferably in the range from 60° to 120° C. A particularly preferred temperature range is from 60° to 90° C.

The reaction can be catalysed by the addition of a minor amount of a protonic acid such as p-toluenesulfonic acid, methanesulfonic acid, sulfuric acid or hydrochloric acid; or of a Lewis acid such as borotrifluoride etherate or aluminium chloride.

The amount of catalyst is 0.01 to 5 mol %, preferably 0.1 to 1.0 mol %, based on the phenol of formula V.

The compounds of formula VII can be obtained in their tautomeric forms of formula VIIa or formula VIIb

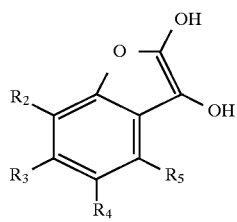

(VIIa)

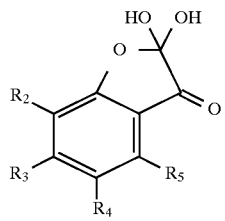

(VIIb)

as described by H. Sterk et al., Monatshefte für Chemie 99, 2223 (1968). Within the scope of this application, formula VII will always be understood as also embracing the two tautomeric formulae VIIa and VIIb.

Bisphenols of formula XIV

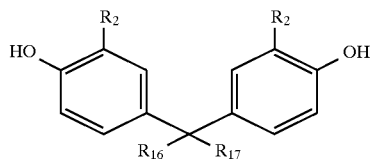

(XV)

can be prepared in accordance with Houben-Weyl, Methoden der organischen Chemie, Vol. 6/1c, 1030.

The compounds of formula I, wherein $R_6$ is hydrogen, can also be prepared by a so-called one-pot process starting from the phenols of formula V, which comprises reacting one equivalent of the phenol of formula VII with 0.8 to 2.0 equivalents of glyoxylic acid to a compound of formula VII, and subsequently reacting said compound of formula VII, without isolation, with a compound of formula VIII.

The definitions of the general symbols in connection with the inventive one-pot process are the same as for the inventive processes discussed previously.

The preferred reaction parameters for the one-pot process correspond to those previously discussed in detail in connection with the two single steps.

Prior to the further reaction with a compound of formula VIII, the 3-hydroxy-3H-benzofuran-2-ones of formula VII initially formed in the one-pot process can be subjected to an additional reaction step by substituting the hydroxyl group with halogen or activating it with a leaving group.

A special one-pot process for the preparation of compounds of formula I comprises using a compound of formula V that differs from the compound of formula VIII.

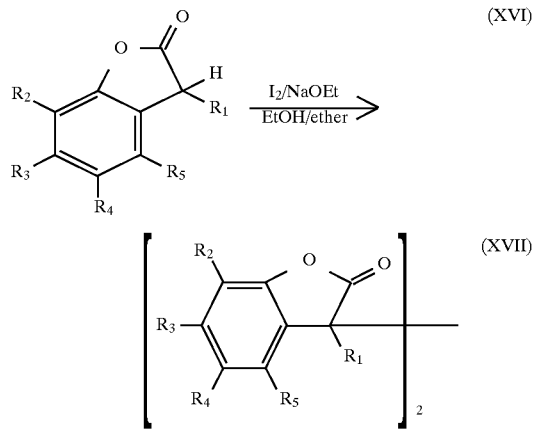

The dimerisation of the compounds of formula XVI for the preparation of compounds of formula I, wherein $R_6$ is a radical of formula IV [compounds of formula XVII] is carried out by oxidation with e.g. iodine under basic conditions in an organic solvent at room temperature. A particularly suitable base is sodium ethylate, and a particularly suitable solvent is ethanol or diethyl ether.

The compounds of formula I are suitable for stabilising organic materials against thermal, oxidative or light-induced degradation.

Illustrative examples of such materials are:
1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrile/vinyl halide copolymers or acrylonitrile/ alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyl resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyl resins, polyester resins and acrylate resins crosslinked with melamine resins, urea resins, polyisocyanates or epoxy resins.
26. Crosslinked epoxy resins derived from polyepoxides, for example from bisglycidyl ethers or from cycloaliphatic diepoxides.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA. PVC/ABS, PVC/MBS, PC/ABS, PBTP/ABS, PC/ASA, PCIPBT, PVC/CPE, PVC/acrylates, POM/thermoplastic PUR, PC/Lhermoplastic PUR, POM/acrylate, POM/MBS, PPO/HIPS, PPO/PA 6.6 and copolymers, PA/HDPE, PA/PP, PA/PPO.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.

Further objects of the invention are therefore also compositions comprising an organic material that is susceptible to oxidative, thermal or light-induced degradation, and at least one compound of formula I.

Preferred organic materials are natural, semi-synthetic or, preferably, synthetic polymers.

Particularly preferred organic materials are synthetic polymers, most preferably thermoplastic polymers. Especially preferred organic materials are polyacetals or polyolefins such as polypropylene or polyethylene.

To be singled out for special mention is the efficacy of the novel compounds against thermal and oxidative degradation, especially under the action of heat which occurs during the processing of thermoplasts. The compounds of this invention are therefore admirably suited for use as processing stabilisers.

The compounds of formula I will preferably be added to the organic material to be stabilised in concentrations of 0.0005 to 5%, preferably 0.001 to 2%, typically 0.01 to 2%, based on the weight of said material.

In addition to comprising the compounds of formula I, the inventive compositions may comprise further co-stabilisers, typically the following:
1. Antioxidants
   1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl) phenol, 2,4-dimethyl-6-(1'-methyltridec-1'-yl)phenol and mixtures thereof.
   1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.
   1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-di-phenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.
   1.4. Tocopherols, for example α-tocopherol, β-tocopherol, γ-tocopherol, δ-tocopherol and mixtures thereof (Vitamin E).
   1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.
   1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylene-bis(6-nonyl-4-methylphenol), 2,2'-methylenebis(4,6-di-tert-butylphenol), 2,2'-ethylidene-bis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-te-t-butylphenol), 4,4'-methylenebis(6-tert-butyl-2-methylphenol), 1,1-bis(5-tert-butyl-4-hydroxy-2-methylphenyl)butane, 2,6-bis(3-tert-butyl- 5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl] terephthalate, 1,1-bis-(3 ,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl) pentane.
   1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-Tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonane-diol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl- 4-hydroxyphenylpropionyl) trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5 '-(2-octyloxycarbonylethyl) phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$], where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4- hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β,-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3, 5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4- piperidyl)-1,2,3,4-butane-tetracarboxylate, 1,1 '-(1, 2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert- butylbenzyl)malonate, 3-n-octyl-7,7,9,9-tetramethyl-1,3,8-triazasprio[4.5]decan-2,4-dion, bis (1-octyloxy-2,2,6,6-tetramethylpiperidyl)sebacate, bis (1-octyloxy-2,2,6,6-tetramethylpiperidyl)succinate, the condensate of N,N'-bis-(2,2,6,6-tetramethyl-4-piperidyl)hexamethylenediamine and 4-morpholino-2, 6-dichloro-1,3,5-triazine, the condensate of 2-chloro-4,6-bis(4-n-butyl-amino-2,2,6,6-tetramethylpiperidyl)-1,3,5-triazine and 1,2-bis(3-aminopropylamino)ethane, the condensate of 2-chloro-4,6-di-(4-n-butylamino-1,2, 2,6,6-pentamethylpiperidyl)-1,3,5-triazine and 1,2-bis-(3-aminopropylamino)ethane, 8-acetyl-3-dodecyl-7,7, 9,9-tetramethyl-1,3,8-triazaspiro[4.5]decane-2,4-dione, 3-dodecyl- 1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-diethoxyanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)- 1,3,5-triazine, 2,4-bis(2-hydroxy-4-propyloxyphenyl)-6-(2, 4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2, 4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene) oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis (2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythiritol diphosphite, bis(2,4,6-tris(tert-butylphenyl) pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenzid[g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, potyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighteners, flameproofing agents, antistatic agents and blowing agents.

The co-stabilisers are typically used in concentrations of 0.01 to 10%, based on the total weight of the material to be stabilised.

The novel compounds of formula I can be used in particular together with phenolic antioxidants, light stabilisers and/or processing stabilisers.

It is particularly preferred to use the novel compounds of formula I together with phenolic antioxidants. The novel compositions therefore preferably comprise, in addition to compounds of formula I, phenolic antioxidants, preferably those listed in items 1.1 to 1.17 of the above list.

Other preferred compositions comprise, in addition to compounds of formula I, a compound of of the organic phosphite or phosphonite type.

The compounds of formula I and other optional additives are incorporated into the organic polymeric material by known methods, conveniently before or during shaping to moulded articles or alternatively by coating the organic polymeric material with a solution or dispersion of the compounds and subsequently evaporating the solvent. The compounds of formula I can also be added to the materials to be stabilised in the form of a masterbatch which contains these compounds, typically in a concentration of 2.5 to 25% by weight.

The compounds of formula I can also be added before or during polymerisation or before crosslinking.

In this connection, particular attention is drawn to the surprising feature that the novel compounds of formula I inhibit discolouration, especially so-called "pinking", in the manufacture of e.g. polyurethane foams.

The compounds of formula I can be incorporated into the material to be stabilised in pure form or in waxes, oils or polymer encapsulations.

The compounds of formula I can also be sprayed on to the polymer to be stabilised. They are able to dilute other additives (typically the conventional additives listed above) or melts thereof, so that they can also be sprayed together with these additives on to the polymer to be stabilised. Application by spraying during deactivation of the polymerisation catalysts is especially advantageous, in which case spraying is conveniently effected with the vapour used for deactivation.

It may be expedient to spray the compounds of formula I, with or without other additives, on to spherical polymerised polyolefins.

A preferred embodiment of this invention is therefore the use of compounds of formula I for stabilising organic materials against oxidative, thermal or light-induced degradation.

The stabilised materials may be in any form of presentation, typically sheets, filaments, ribbons, mouldings, profiles or binders for coating compositions, adhesives or putties.

The invention also relates to a process for stabilising an organic material against oxidative, thermal or light-induced degradation, which comprises incorporating therein or applying thereto at least one compound of formula I.

As already emphasised, the novel compounds are used with particular advantage as stabilisers in polyolefins, preferably as heat stabilisers. Excellent stabilisation is achieved when the compounds are used in conjunction with organic phosphites or phosphonites. The novel compounds have in this case the advantage that they are effective in exceedingly low concentration, typically in concentrations from 0.0001 to 0.050% by weight, preferably from 0.0001 to 0.015% by weight, based on the polyolefin. The organic phosphite or phosphonite is conveniently used in a concentration of 0.01 to 2% by weight, preferably of 0.01 to 1% by weight, based on the polyolefin. It is preferred to use the organic phosphites and phosphonites disclosed in DE-A-4 202 276. Attention is drawn in particular to the claims, to the Examples and to pages 5, last paragraph, to 8. Particularly suitable phosphites and phosphonites will also be found under item 4 of the above list of co-stabilisers.

Some of the novel compounds of formula I, when incorporated in polyolefins, induce slight yellowing. This yellowing of polyolefins can be substantially inhibited by a combination of the novel compounds of formula I with phosphites or phosphonites.

Further objects of the invention are compositions comprising a functional fluid, preferably of the series of the lubricants, hydraulic fluids and metal processing fluids as well as fuels for driving motors of the Otto 4-stroke, Otto 2-stroke, diesel, Wankel and orbital type, and at least one compound of formula I.

Particularly preferred lubricants are the mineral oils, the synthetic oils or mixtures thereof.

Suitable functional fluids of the series of the lubricants, hydraulic fluids and metal processing fluids are per se known products.

The suitable lubricants and hydraulic fluids are known to the skilled person and are described in the relevant literature, inter alia in Dieter Klamann, "Schmierstoffe und verwandte Produkte" (Lubricants and Related Products) (Verlag Chemie, Weinheim, 1982), in Schewe-Kobek, "Das Schmiermittel-Taschenbuch" (Handbook of Lubricants) (Dr. Alfred Hüthig-Verlag, Heidelberg, 1974), and in "Ullmanns Enzyklopädie der technischen Chemie" (Ullmann's Encyclopedia of Industrial Chemistry), Vol. 13, pages 85–94 (Verlag Chemie, Weinheim, 1977).

Illustrative examples are lubricants and hydraulic fluids based on mineral oils or synthetic lubricants or hydraulic fluids, especially those that are carboxylic acid derivatives and are used at temperatures of 200° C. and above.

Synthetic lubricants typically comprise lubricants based on a diester of a divalent acid with a monohydric alcohol, typically dioctyl sebacate or dinonyl adipate, on a triester of trimethylolpropane with a monovalent acid or with a mixture of acids, conveniently trimethylolpropane tripelargonate, trimethylolpropane tricaprylate or mixtures thereof, on a tetraester of pentaerythritol with a monovalent acid or with a mixture of such acids, typically pentaerythritol tetracaprylate, or on a complex ester of monovalent and divalent acids with polyhydric alcohols, for example a complex ester of trimethylolpropane with caprylic and sebacic acid or of a mixture thereof.

Especially suitable lubricants are, in addition to mineral oils, typically poly-α-olefins, ester-based lubricants, phosphates, glycols, polyglycols and polyalkylene glycols and mixtures thereof with water.

The compounds of formula I are readily soluble in lubricants and are therefore especially suitable for use as additives for lubricants. Their surprisingly good antioxidative and anticorrosive properties merit special mention.

In lubricants for combustion engines, as in combustion engines that operate according to the Otto principle, the novel compounds of formula I are able to exert their surprising properties. Thus the compounds of formula I inhibit in lubricant oils the formation of deposits (sludge) or reduce such deposits in surprising manner.

It is also possible to prepare masterbatches.

The compounds of formula I act as additives in lubricants even in very minor amounts. They are conveniently added to the lubricants in an amount of 0.01 to 5% by weight, preferably of 0.05 to 3% by weight and, most preferably, of 0.1 to 2% by weight, based in each case on the lubricant.

The lubricants may also contain other additives which are added for further enhancement of the basic properties. These further additives comprise antioxidants, metal deactivators, rust inhibitors, viscosity improvers, pour-point depressants, dispersants, detergents, other extreme-pressure and antiwear additives.

A number of such compounds will be found in the above list under item "1. Antioxidants", especially under 1.1 to 1.17. Illustrative examples of such further additives are:

Examples of aminic antioxidants:

N,N'-diisopropyl-p-phenylenediamine, N,N'-di-sec-butyl-p-phenylenediamine, N,N'-bis-(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethyl-butyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methyl-phenyl)amino]ethane, 1,2-bis-(phenylamino) propane, (o-tolyl)biguanide, bis[4-(1',3'-dimethylbutyl) phenyl]amine, tertoctylated N-phenyl-1-naphthylamine, a mixture of mono- and dialkylated tert-butyl/tert-octyldiphenylamines, a mixture of mono- and dialkylated isopropyllisohexyldiphenylamines, mixtures of mono- and dialkylated tert-butyldiphenylamines, 2,3-dihydro-3,3-dimethyl-4H-1,4-benzothiazine, phenothiazine, N-allylphenothiazine, N,N,N',N'-tetra-phenyl-1,4-diaminobut-2-ene, N,N-bis(2,2,6,6-tetramethylpiperid-4-yl-hexamethylenediamine, bis(2,2,6,6-tetramethylpiperid-4-yl) sebacate, 2,2,6,6-tetramethylpiperidin-4-one and 2,2,6,6-tetramethylpiperidin-4-ol.

Examples of other antioxidants:

Aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,11-trithiatridecane and 2,2,15,15-tetramethyl-5,12-dihydroxy-3,7,10,14-tetrathiahexadecane.

Examples of metal deactivators, for example for copper, are:

a) Benzotriazoles and derivatives thereof, for example 4- or 5-alkylbenzotriazoles (e.g. tolulriazole) and derivatives thereof, 4,5,6,7-tetrahydrobenzotriazole and 5,5'-methylenebisbenzotriazole; Mannich bases of benzotriazole or tolutriazole, e.g.

1-[bis(2-ethylhexyl)aminomethyl)tolutriazole and 1-[bis (2-ethylhexyl)aminomethyl)benzotriazole; and alkoxyalkylbenzotriazoles such as 1-(nonyloxymethyl)benzotriazole, 1-(1-butoxyethyl)benzotriazole and 1-(1-cyclohexyloxybutyl)tolutriazole.

b) 1,2,4-Triazoles and derivatives thereof, for example 3-alkyl(or aryl)-1,2,4-triazoles, and Mannich bases of 1,2,4-triazoles, such as 1-[bis(2-ethylhexyl)aminomethyl-1,2,4-triazole; alkoxyalkyl-1,2,4-triazoles such as 1-(1-butoxyethyl)- 1,2,4-triazole; and acylated 3-amino-1,2,4-triazoles.

c) Imidazole derivatives, for example 4,4'-methylenebis (2-undecyl-5-methylimidazole) and bis[(N-methyl) imidazol-2-yl]carbinol octyl ether.

d) Sulfur-containing heterocyclic compounds, for example 2-mercaptobenzothiazole, 2,5-dimercapto-1,3,4-thiadiazole and derivatives thereof; and 3,5-bis[di(2-ethylhexyl)aminomethyl]-1,3,4-thiadiazolin-2-one.

e) Amino compounds, for example salicylidenepropylenediamine, salicylaminoguanidine and salts thereof.

Examples of rust inhibitors are:

a) Organic acids, their esters, metal salts, amine salts and anhydrides, for example alkyl- and alkenylsuccinic acids and their partial esters with alcohols, diols or hydroxycarboxylic acids, partial amides of alkyl- and alkenylsuccinic acids, 4-nonylphenoxyacetic acid, alkoxy- and alkoxyethoxycarboxylic acids such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-(carboxyethyl)-1-dodecyl-3-methylglycerol and the amine salts thereof.

b) Nitrogen-containing compounds, for example:

I. Primary, secondary or tertiary aliphatic or cycloaliphatic amines and amine salts of organic and inorganic acids, for example oil-soluble alkylammonium carboxylates, and also 1-[N,N-bis(2-hydroxyethyl)amino]-3-(4-nonylphenoxy)propan-2-ol.

II. Heterocyclic compounds, for example: substituted imidazolines and oxazolines, and 2-heptadecenyl-1-(2-hydroxyethyl)imidazoline.

c) Phosphorus-containing compounds, for example:

Amine salts of phosphoric acid partial esters or phosphonic acid partial esters, and zinc dialkyldithiophosphates.

d) Sulfur-containing compounds, for example: barium dinonylnaphthalenesulfonates, calcium petroleum sulfonates, alkylthio-substituted aliphatic carboxylic acids, esters of aliphatic 2-sulfocarboxylic acids and salts thereof.

e) Glycerol derivatives, for example: glycerol monooleate, 1-(alkylphenoxy)-3-(2-hydroxyethyl)glycerols, 1-(alkylphenoxy)-3-(2,3-dihydroxypropyl)glycerols and 2-carboxyalkyl-1,3-dialkylglycerols.

Examples of viscosity index improvers are:

Polyacrylates, polymethacrylates, vinylpyrrolidone/methacrylate copolymers, polyvinylpyrrolidones, polybutenes, olefin copolymers, styrene/acrylate copolymers and polyethers.

Examples of pour-point depressants are:

Polymethacrylate and alkylated naphthalene derivatives.

Examples of dispersants/surfactants are:

Polybutenylsuccinic amides or -imides, polybutenylphosphonic acid derivatives and basic magnesium, calcium and barium sulfonates and phenolates.

Examples of antiwear additives are:

Sulfur- and/or phosphorus- and/or halogen-containing compounds, e.g. sulfurised olefins and vegetable oils, zinc dialkyldithiophosphates, alkylated triphenyl phosphates, tritolyl phosphate, tricresyl phosphate, chlorinated paraffins, alkyl and aryl di- and trisulfides, amine salts of mono- and dialkyl phosphates, amine salts of methylphosphonic acid, diethanolaminomethyltolyltriazole, bis(2-ethylhexyl) aminomethyltolyltriazole, derivatives of 2,5-dimercapto-1,3,4-thiadiazole, ethyl 3-[(diisopropoxyphosphinothioyl) thio]propionate, triphenyl thiophosphate (triphenylphosphorothioate), tris(alkylphenyl) phosphorothioate and mixtures thereof (for example tris (isononylphenyl) phosphorothioate), diphenyl mononylphenyl phosphorothioate, isobutylphenyl diphenyl phosphorothioate, the dodecylamine salt of 3-hydroxy-1,3-thiaphosphetane 3-oxide, trithiophosphoric acid 5,5,5-tris [isooctyl 2-acetate], derivatives of 2-mercaptobenzothiazole such as 1-[N,N-bis-(2-ethylhexyl)aminomethyl]-2-mercapto-1H-1,3-benzothiazole, and ethoxycarbonyl-5-octyldithiocarbamate.

The invention is illustrated in more detail by the following Examples, in which parts and percentages are by weight.

EXAMPLE 1

Preparation of 5,7-di-tert-butyl-3-(2,5-dimethylphenyl)-3H-benzofuran-2-one (compound (101), Table 1) starting from 5,7-di-tert-butyl-3-hydroxy-3H-benzofuran-2-one (compound (201), Table 2) with p-xylene, as well as Fulcat 22B as catalyst.

a) Preparation of 5,7-di-tert-butyl-3-hydroxy-3H-benzofuran-2-one (compound (201), Table 2).

A mixture of 212.5 g (1.00 mol) of 2,4-di-tert-butylphenol (97%), 163.0 g (1.10 mol) of 50% aqueous glyoxylic acid and 0.5 g (2.6 mmol) of p-toluenesulfonic acid monohydrate in 300 ml of 1,2-dichloroethane is refluxed under nitrogen for 3.5 hours on a water separator. Afterwards the reaction mixture is concentrated on a vacuum rotary evaporator. The residue is taken up in 800 ml of hexane and washed three times with water. The aqueous phases are separated in the separating funnel and further extracted with 300 ml of hexane. The organic phases are combined, dried over magnesium sulfate and concentrated on a vacuum rotary evaporator. The residue yields 262.3 g (~100%) of analytically pure 5,7-di-tert-butyl-3-hydroxy-3H-benzofuran-2-one in the form of a thick yellowish resin (compound (201), Table 2).

In analogy to Example 1a, compounds (202), (203), (204), (205), (209), (210) and (211) are prepared from the corresponding phenols such as 2-tert-butyl-4-methylphenol, 4-tert-butyl-2-methylphenol, 2,4-dicyclohexylphenol, 2-(hexadec-2-yl)-4-methylphenol, 3-[3-tert-butyl-4-hydroxyphenyl]propionic acid, 2,4-bis($\alpha$,$\alpha$-dimethylbenzyl)phenol and 4-methyl-2-(1,1,3,3-tetramethylbut-1-yl)phenol with glyoxytic acid. To prepare compound (207), 2 equivalents of glyoxylic acid are used starting from 1,1-bis(3-tert-butyl-4-hydroxyphenyl) cyclohexane.

b) Preparation of 5,7-di-tert-butyl-3-(2,5-dimethylphenyl)-3H-benzofuran-2-one (compound (101), Table 1)

To a solution of 262.3 g (1.00 mol) of 5,7-di-tert-butyl-3-hydroxy-3H-benzofuran-2-one (compound (201), Table 2, Example 1a) in 500 ml (4.05 mol) of p-xylene are added 40 g of Fulcat 22B and the mixture is refluxed for 1.5 hours on a water separator. The Fulcat 22B catalyst is then removed by filtration and excess p-xylene is removed by distillation on a vacuum rotary evaporator. Crystallisation of the residue from 400 ml of methanol yields 280.6 g (80%) of 5,7-di-tert-butyl-3-(2,5-dimethylphenyl)-3H-benzofuran-2-one, m.p. 93°–97° C. (compound (101), Table 1).

EXAMPLE 2

Preparation of 5,7-di-tert-butyl-3-(2,5-dimethylphenyl)-3H-benzofuran-2-one (compound (101), Table 1) starting from 3-acetoxy-5,7-di-tert-butyl-3H-benzofuran-2-one (compound (206), Table 2) with p-xylene, as well as Fulcat 22B as catalyst.

a) Preparation of 3-acetoxy-5,7-di-tert-butyl-3H-benzofuran-2-one (compound (206), Table 2).

A mixture of 21.2 g (0.10 mol) of 2,4-di-tert-butylphenol (97%), 16.3 g (0.11 mol) of 50% aqueous glyoxylic acid and 0.05 g (0.26 mmol) of p-toluenesulfonic acid monohydrate in 30 ml of 1,2-dichloroethane is refluxed under nitrogen for 3.5 hours on a water separator. Afterwards the reaction mixture is concentrated on a vacuum rotary evaporator. The residue is taken up in 9.9 ml (0.105 mol) of acetic anhydride and the solution is refluxed for 90 minutes. The reaction mixture is then cooled to room temperature, diluted with 100 ml of tert-butyl methyl ether and washed in succession with water and dilute sodium hydrogencarbonate solution. The aqueous phases are separated and extracted with 50 ml of tert-butyl methyl ether. The organic phases are combined, dried over magnesium sulfate and concentrated on a vacuum rotary evaporator. Chromatography of the residue on silica gel with the solvent system dichloromethane/hexane=2:1 yields 28.0 g (92%) of 3-acetoxy-5,7-di-tert-butyl-3H-benzofuran-2-one (compound (206), Table 2) as a thick reddish resin.

b) Preparation of 5,7-di-tert-butyl-3-(2,5-dimethylphenyl)-3H-benzofuran-2-one (compound (101), Table 1)

To a solution of 15.3 g (50.0 mmol) of 3-acetoxy-5,7-di-tert-butyl-3H-benzofuran-2-one (compound (206), Table 2, Example 2a) in 25 ml (0.20 mol) of p-xylene is added 1.0 g of Fulcat 22B and the mixture is refluxed for 17 hours on a water separator. The Fulcat 22B catalyst is then removed by filtration and excess p-xylene is removed by distillation on a vacuum rotaray evaporator. Crystallisation of the residue from 20 ml of methanol yields 10.5 g (60%) of 5,7-di-tert-butyl-3-(2,5-dimethylphenyl)-3H-benzofuran-2-one, m.p. 93°–97° C. (compound (101), Table 1).

EXAMPLE 3

Preparation of 3-(3,4-dimethylphenyl)-5,7-di-tert-butyl-3H-benzofuran-2-one (compound (103), Table 1) starting from 5,7-di-tert-butyl-3-hydroxy-3H-benzofuran-2-one (compound (201), Table 2) with o-xylene, as well as Fulcat 22B as catalyst.

To a solution of 262.3 g (1.00 mol) of 5,7-di-tert-butyl-3-hydroxy-3H-benzofuran-2-one (compound (201), Table 2, Example 1a) in 500 ml (4.05 mol) of o-xylene are added 40 g of Fulcat 22B and the mixture is refluxed for 1.5 hours on a water separator. The Fulcat 22B catalyst is then removed by filtration and excess p-xylene is removed by distillation on a vacuum rotary evaporator. Crystallisation of the residue from 500 ml of methanol yields 244 g (69%) of 3-(3,4-dimethylphenyl)-5,7-di-tert-butyl)-3H-benzofuran-2-one, m.p. 130°–132° C. (compound (103), Table 1), which additionally contains c. 1.3% of the structural isomer [3-(2,3-dimethylphenyl)-5,7-di-tert-butyl-3H-benzofuran-2-one, compound (103A)]. The mother liquor yields a further 42.4 g of product which, according to GC-MS analysis, consists of 12.3% of the compound (103) and 87.7% of the isomeric compound (103A).

EXAMPLE 4

Preparation of 5,7-di-tert-butyl-3-(4-ethylphenyl)-3H-benzofuran-2-one (compound (105), Table 1) starting from 5,7-di-tert-butyl-3-hydroxy-3H-benzofuran-2-one (compound (201), Table 2, with ethyl benzene, as well as Fulcat 22B as catalyst.

To a solution of 262.3 g (1.00 mol) of 5,7-di-tert-butyl-3-hydroxy-3H-benzofuran-2-one (compound (201), Table 2, Example 1a) in 500 ml (4.08 mol) of ethyl benzene are added 40 g of Fulcat 22B and the mixture is refluxed for 1.5 hours on a water separator. The Fulcat 22B catalyst is then removed by filtration and excess ethyl benzene is removed by distillation on a vacuum rotary evaporator. GC-MS analysis shows the residue to consist of a mixture of 59.2% of the para-isomer (compound (105), Table 1), 10.8% of the meta-isomer (compound (IOSA) and 21.1% of the ortho-isomer(compound (105B). Crystallisation of the residue from 400 ml of methanol yields 163.8 g (47%) of 5,7-di-tert-butyl)-3-(4-ethylphenyl)-3H-benzofuran-2-one (compound (105), Table 1) (para-isomer), which additionally contains 5.6% of the meta-isomer 5,7-di-tert-butyl-3-(3-ethylphenyl)-3H-benzofuran-2-one (compound (USA) and 1.3% of the ortho-isomer 5,7-di-tert-butyl- 3-(2-ethylphenyl)3H-benzofuran-2-one (compound (105B). Further crystallisation from methanol yields the almost pure para-isomer (compound (105), Table 1), m.p. 127°–132° C.

In accordance with the general procedure described in this Example, compounds (102), (106), (107), (114), (115), (116), (117), (118) and (119) are prepared from 5,7-di-tert-butyl-3-hydroxy-3H-benzofuran-2-one (compound (201), Table 2, Example 1a) and the corresponding aromatic hydrocarbons, typically including m-xylene, isopropylbenzene (cumene), tert-butylbenzene, biphenyl, thiophene, p-xylene, dibenzofuran, phenanthrene and diphenyl ether. To prepare compound (119), 2 equivalents of 5,7-di-tert-butyl-3-hydroxy-3H-benzofuran-2-one are used starting from diphenyl ether.

EXAMPLE 5

Preparation of 5,7-di-tert-butyl-3-(2,3,4,5,6-pentamethylphenyl)-3H-benzofuran-2-one (compound (111), Table 1) starting from 5,7-di-tert-butyl-3-hydroxy-3H-benzofuran-2-one (compound (201), Table 2) with pentamethylbenzene, as well as tin tetrachloride as catalyst.

11.5 g (77.5 mmol) of pentamethylbenzene and 10 ml (85.0 mmol) of tin tetrachloride are added to a solution of 19.7 g (75.0 mmol) of 5,7-di-tert-butyl-3-hydroxy-3H-benzofuran-2-one (compound (201), Table 2, Example 1a) in 50 ml of 1,2-dichloroethane and the reaction mixture is refluxed for 1 hour. The reaction mixture is diluted with water and extracted three times with toluene. The organic phases are combined, washed with water, dried over sodium sulfate and concentrated on a vacuum rotary evaporator. Crystallisation of the residue from ethanol yields 26.3 g (89%) of 5,7-di-tert-butyl-3-(2,3,4,5,6-pentamethylphenyl)-3H-benzofuran-2-one, m.p. 185°–190° C. (compound (111), Table 1).

In accordance with the general procedure of this Example, compounds (109) and (110) are prepared from 5,7-di-tert-butyl-3-hydroxy-3H-benzofuran-2-one (compound (201), Table 2, Example 1a) and the corresponding aromatic hydrocarbons, for example n-dodecylbenzene and 1,2,3-trimethylbenzene.

EXAMPLE 6

Preparation of 5,7-di-tert-butyl-3-(4-methylthiophenyl)-3H-benzofuran-2-one (compound (108), Table 1) starting from 5,7-di-tert-butyl-3-hydroxy-3H-benzofuran-2-one (compound (201), Table 2) with thioanisole, as well as aluminium trichloride as catalyst.

A solution of 26.2 g (0.10 mol) of 5,7-di-tert-butyl-3-hydroxy-3H-benzofuran-2-one (compound (201), Table 2, Example 1a) in 25 ml (0.21 mol) of thioanisole is added dropwise to a solution of 14.7 g (0.11 mol) of aluminium chloride in 15 ml (0.13 mol) of thioanisole at 35°–40° C. The reaction mixture is thereafter stirred for 30 minutes at 30° C. and for 2 hours at 80° C., and then after cooling, c. 50 ml of water and then concentrated hydrochloric acid and methylene chloride are added cautiously in sufficient amount to form a homogeneous two-phase mixture. The organic phase is separated, washed with water, dried over sodium sulfate and concentrated on a vacuum rotary evaporator. Crystallisation of the residue from ethanol yields 6.7 g (18%) of 5,7-di-tert-butyl-3-(4-methylthiophenyl)-3H-benzofuran-2-one, m.p. 125°–131° C. (compound (108), Table 1).

EXAMPLE 7

Preparation of 5,7-di-tert-butyl-3-(4-methylphenyl)-3H-benzofuran-2-one (compound (104), Table 1) starting from 2,4-di-tert-butylphenol, without isolation of 5,7-di-tert-butyl-3-hydroxy-3H-benzofuran-2-one (compound (201), Table 2), with glyoxylic acid and toluene, as well as Fulcat 22B as catalyst.

A mixture of 21.2 g (0.10 mol) of 2,4-di-tert-butylphenol (97%), 16.3 g (0.11 mol) of 50% aqueous glyoxylic acid, 2.0 g of Fulcat 22B and 50 ml of toluene is refluxed for 8 hours under nitrogen on a water separator. The Fulcat 22B catalyst is then removed by filtration and excess toluene is distilled off on a vacuum rotary evaporator. Crystallisation of the residue from 40 ml of ethanol yields 14.2 g (42%) of 5,7-di-tert-butyl-3-(4-methylphenyl)-3H-benzofuran-2-one, m.p. 130°–133° C. (compound (104), Table 1).

In accordance with the general procedure of this Example, the compound (112) is prepared starting from 2-tert-butyl-4-methylphenol instead of from 2,4-di-tert-butylphenol.

EXAMPLE 8

Preparation of 4,4'-di-(5,7-di-tert-butyl-3H-benzofuran-2-on-3-yl)-N-methyldiphenylamine (compound (113), Table 1) starting from 5,7-di-tert-butyl-3-hydroxy-3H-benzofuran-2-one (compound (201), Table 2) with N-methyl-diphenylamine, as well as p-toluenesulfonic acid as catalyst.

30.2 g (115.0 mmol) of 5,7-di-tert-butyl-3-hydroxy-3H-benzofuran-2-one (compound (201), Table 2, Example 1a) are added over 2 hours to a boiling solution of 9.20 g (50.0 mmol) of N-methyl-diphenylamine and 0.20 g of p-toluenesulfonic acid monohydrate in 50 ml of ligroin (mixture of alkanes with a boiling range of 140°–160° C.). The reaction mixture is then refluxed for 4 hours on a water separator, then cooled and concentrated on a vacuum rotary evaporator. Crystallisation of the residue from isopropanol/water=9:1 yields 18.9 g (56%) of 4,4'-bis(5,7-di-tert-butyl-3H-benzofuran-2-on-3-yl)-N-methyl-diphenylamine, m.p. 135°–145° C. (compound (113), Table 1).

EXAMPLE 9

Preparation of 7-tert-butyl-5-methyl-3-(9-methyl-9H-carbazol-3-yl)-3H-benzofuran-2-one (compound (120), Table 1) starting from 7-tert-butyl-3-hydroxy-5-methyl-3H-benzofuran-2-one (compound (202), Table 2) with N-methylcarbazole and n-octane, as well as Fulcat 22B as catalyst.

A mixture of 2.2 g (10.0 mmol) of 7-tert-butyl-3-hydroxy-5-methyl-3H-benzofuran-2-one (compound (202), Example 1a, Table 2), 1.8 g (10.0 mmol) of N-methylcarbazole and 0.2 g of Fulcat 22B and 20 ml of n-octane is refluxed for 5 hours under nitrogen. The Fulcat 22B catalyst is subsequently removed by filtration and excess n-octane is distilled off on a vacuum rotary evaporator. Chromatography of the residue on silica gel with the solvent system dichloromethan/hexane=1:2 to 1:1 and subsequent crystallisation of the pure fractions from methanol yields 0.70 g (10%) of 7-tert-butyl-5-methyl-3-(9-methyl-9H-carbazol-3-yl)-3H-benzofuran-2-one, m.p. 84°–90° C. (compound (120), Table 1). The product may additionally contain minor amounts of other structural isomers in accordance with the substitution at the carbazole ring.

EXAMPLE 10

Preparation of 5,7-di-tert-butyl-3-(9H-fluoren-3-yl)-3H-benzofuran-2-one (compound (121), Table 1) starting from 2,4-di-tert-butylphenol, without isolation of 5,7-di-tert-butyl-3-hydroxy-3H-benzofuran-2-one (compound (201), Table 2), with glyoxylic acid and fluorene, as well as p-toluenesulfonic and Fulcat 22B as catalyst.

A mixture of 15.9 g (75 mmol) of 2,4-di-tert-butylphenol (97%), 12.2 g (82 mmol) of 50% aqueous glyoxylic acid, 40 mg (0.20 mmol) of p-toluenesulfonic acid monohydrate and 25 ml of 1,2-dichloroethane is refluxed for 3.5 hours under nitrogen on a water separator. The reaction mixture is thereafter concentrated on a vacuum rotary evaporator. The residue is dissolved in 30 ml of n-octane and 12.5 g (75 mmol) of fluorene and 3 g of Fulcat 22B are added to the solution. This reaction mixture is refluxed for 3.5 hours under nitrogen on a water separator, then cooled and filtered. The filtrate is concentrated on a vacuum rotary evaporator. Chromatography of the residue on silica gel with the solvent system dichloromethane/hexane=2:1 and subsequent crystallisation of the pure fractions from methanol yields 5.28 g (17%) of 5,7-di-tert-butyl-3-(9H-tuoren-3-yl)-3H-benzofuran-2-one, m.p. 140°–153° C. (compound (121), Table 1). The product may additionally contain minor amounts of other structural isomers in accordance with the substitution at the fluorene ring.

EXAMPLE 11

Preparation of a c. 5.7:1 mixture of 3-(3,4-dimethylphenyl)-5,7-di-tert-butyl-3H-benzofuran-2-one (compound (103), Table 1) and 3-(2,3-dimethylphenyl)-5,7-di-tert-butyl-3H-benzofuran-2-one (compound (103A)) isomers starting from 2,4-di-tert-butylphenol with glyoxylic acid and o-xylene, as well as Fulcat or Fulmont as catalyst.

To a 1500 ml double-walled reactor with water separator are charged 206.3 g (1.0 mol) of 2,4-di-tert-butylphenol, 485 g (5.5 mol) of o-xylene, 0.5 g (2.6 mmol) of p-toluenesulfonic acid monohydrate and 163 g (1.1 mol) of 50% aqueous glyoxylic acid. With stirring, the mixture is heated to 85°–90° C. and the apparatus is simultaneously evacuated to c. 450 mbar. As soon as the temperature in the reactor is 85°–90° C., a mixture of o-xylene/water begins to distill from the mixture, the o-xylene being refluxed and the water removed from the system. The vacuum is then raised continuously so that the temperature in the reactor can be kept at 85°–90° C. Altogether c. 98–100 ml of water are distilled over 3 to 4 hours. The vacuum is then released with nitrogen and 40 g of catalyst (Fulcat 30 or 40, Fulmont XMP-3 or XMP-4) are added to the clear yellow solution. The apparatus is evacuated to a pressure of 700 mbar and the suspension is stirred at a heating bath temperature of 165° C. The water of reaction begins to distill from the system as an azeotrope from a temperature of c. 128° C. The temperature in the apparatus rises towards the end to a maximum of 140° C. A total amount of c. 20 ml of water distills from the system over 1 to 2 hours. The vacuum is then released with nitrogen. The reaction mixture is cooled to 90°–100° C. and filtered. The apparatus and the filter residue are rinsed with 100 g of oxylene. The filtrate is transferred to a 1500 ml double-walled reactor and concentrated under vacuum and 360 g of o-xylene are recovered. The reddish-yellow residue is cooled to 70° C. and 636 g of methanol are added cautiously from a dropping funnel, while keeping the temperature at 60°–65° C. The solution is seeded and stirred for c. 30 minutes at 60°–65° C. to effect crystallisation. The crystalline slurry is then cooled over 2 hours to –5° C. and stirring is continued at this temperature for a further 1 hour. The crystals are collected by suction filtration and the residue is washed with 400 g of cold (–5° C.) methanol in 5 portions. The well dry-pressed product is dried in a vacuum drier at 50°–60° C., yielding 266 g of a white solid. Analysis by gas chromatography shows this material to consist of c. 85% of 3-(3,4-dimethylphenyl)-5,7-di-tert-butyl-3H-benzofuran-2-one (compound (103), Table I) as well as of c. 15% of the 3-(2,3-dimethylphenyt)-5,7-di-tert-butyl-3H-benzofuran-2-one isomer (compound (1(103A)).

EXAMPLE 12

Preparation of 3-(N-methylcarbamoyloxy)-5-methyl-7-tert-butyl-3H-benzofuran- 2-one (compound (212), Table 2).

A mixture of 5.5 g (25.0 mmol) of 7-tert-butyl-3-hydroxy-5-methyl-3H-benzofuran-2-one (compound (202), Example 1a), 3 ml (50.0 mmol) of methyl isocyanate and 2 drops of methanesulfonic acid are refluxed for 3¼ hours. Then a further 3 ml (50.0 mmol) of methyl isocyanate and 2 drops of methanesulfonic acid are added. The reaction mixture is refluxed for another 16 hours, then cooled, diluted with dichloromethane and washed with water and a 5% aqueous solution of sodium hydrogencarbonate. The organic phases are combined, dried over magnesium sulfate and concentrated on a vacuum rotary evaporator. Crystallisation of the residue from toluene yields 4.45 g (65%) of 3-(N-methylcarbamoyloxy)-5-methyl-7-tert-butyl-3H-benzofuran-2-one (compound (212), Table 2), m.p. 138°–143° C. (compound (212), Table 2).

EXAMPLE 13

Preparation of 7-tert-butyl-3-chloro-5-methyl-3H-benzofuran-2-one (compound (208), Table 2).

To a suspension of 2.2 g (10.0 mmol) of 7-tert-butyl-3-hydroxy-5-methyl-3H-benzofuran-2-one (compound (202), Example 1a, Table 2) in 2.4 ml (55.0 mmol) of thionyl chloride is added one drop of dimethyl formamide and the mixture is stirred for 2 hours at room temperature. Excess thionyl chloride is afterwards distilled off on a vacuum rotary evaporator. Chromatography of the residue on silica gel with the solvent system dichloromethane/hexane=1:1 and crystallisation of the pure fractions from methanol yields 0.30 g (13%) of 7-tert-butyl-3-chloro-5-methyl-3H-benzofuran-2-one, m.p. 81°–86° C. (compound (208), Table 2).

TABLE 1

| No. | Compound | m.p. (°C.) | C (%), H (%) (calcd/found) | Yield (%) |
|---|---|---|---|---|
| 101 | | 93–97 | 82.24 8.63<br>82.10 8.66 | 80 |
| 102 | | 92–96 | 82.24 86.3<br>82.19 8.78 | 52[a)] |
| 103 | | 130–132 | 82.24 8.63<br>82.36 8.62 | 69[a)] |
| 104 | | 130–133 | 82.10 8.39<br>82.13 8.31 | 42[a)] |
| 105 | | 127–132 | 82.24 8.63<br>82.39 8.65 | 47[a)] |
| 106 | | 109–115 | 82.37 8.85<br>82.24 8.91 | 41[a)] |

TABLE 1-continued

| | Structure | mp (°C) | NMR data | Yield |
|---|---|---|---|---|
| 107 | (3,5-di-tert-butyl-2-methylphenyl)(4-tert-butylphenyl)acetic acid | 110–115 | 82.49  9.05<br>82.49  9.03 | 68[a)] |
| 108 | (3,5-di-tert-butyl-2-methylphenyl)(phenyl)acetic acid | 125–131 | characterised by<br>$^1$H-NMR (CDCl$_3$)<br>δ(H*) = 4.79 ppm | 18[a)] |
| 109 | (3,5-di-tert-butyl-2-methylphenyl)(4-dodecylphenyl)acetic acid | oil | characterised by<br>$^1$H-NMR (CDCl$_3$)<br>δ(H*) = 4.84 ppm | 66[a)] |
| 110 | (3,5-di-tert-butyl-2-methylphenyl)(2,3,4-trimethylphenyl)acetic acid | 118–122 | 82.37  8.85<br>82.31  8.84 | 74[a)] |
| 111 | (3,5-di-tert-butyl-2-methylphenyl)(pentamethylphenyl)acetic acid | 185–190 | 82.61  9.24<br>82.41  9.43 | 89 |
| 112 | (3-tert-butyl-5-methylphenyl)(4-methylphenyl)acetic acid | 69–80 | 81.60  7.53<br>81.42  7.57 | 70[a)] |

TABLE 1-continued

| No. | Compound | m.p. (°C.) | C (%), H (%), N (%) (calcd/found) | Yield (%) |
|---|---|---|---|---|
| 113 | [structure] | 135–145 | 80.44 7.95 2.08<br>80.20 8.06 1.96 | 56[a] |
| 114 | [structure] | 168–170 | 84.38 7.57<br>84.23 7.66 | 25[a] |
| 115 | [structure] | 86–93 | C (%), H (%), S (%)<br>73.13 7.37 9.76<br>73.10 7.38 9.69 | 11[a] |
| 116 | [structure] | 220–228 | 82.60 7.84<br>82.58 7.85 | 40 |

[a] The product may additionally contain minor amounts of other structural isomers in accordance with the substitution at the phenyl ring in 3-position of the benzofuran-2-one.

| No. | Compound | m.p. (°C.) | C (%), H (%) (calcd/found) | Yield (%) |
|---|---|---|---|---|
| 117 | [structure] | 142–154 | 81.52 6.84<br>80.97 6.5 | 33[a] |

TABLE 1-continued

| No. | Compound | m.p. (°C.) | C (%), H (%) (calcd/found) | Yield (%) |
|---|---|---|---|---|
| 118 | [structure: 3,5-di-tert-butyl-2-methylphenyl group with -CH(H)- attached to phenanthren-2-yl and a C=O-O linkage] | 186–189 | 85.27  7.16<br>85.15  7.20 | 17[a)] |
| 119 | [structure: bis(benzofuranone) linked via 4,4'-oxydiphenyl bridge, each bearing 3,5-di-tert-butyl-2-methylphenyl group] | resin | characterised by<br>¹H-NMR (CDCl₃)<br>δ(H*) = 4.82 ppm | 31[a)] |
| 120 | [structure: 3,5-di-tert-butyl-2-methylphenyl group with -CH(H)- attached to 9-methylcarbazol-3-yl, C=O-O linkage] | 84–90 | 81.43  6,57<br>81.37  6,72 | 10[a)] |

[a)] The product may additionally contain minor amounts of other structural isomers in accordance with the substitution at the aryl ring in 3-position of the benzofuran-2-one.

| 121 | [structure: 3,5-di-tert-butyl-2-methylphenyl group with -CH(H)- attached to a fluorene ring system (biphenyl with CH₂ bridge), C=O-O linkage] | 140–153 | 84.84  7.37<br>84.66  7.52 | 17[a)] |

[a)] The product may additionally contain minor amounts of other structural isomers in accordance with the substitution at the fluorene ring in 3-position of the benzofuran-2-one.

TABLE 2

| No. | Compound | m.p. (°C.) | C (%), H (%) (calcd/found) | Yield (%) |
|---|---|---|---|---|
| 201 | [structure: 3,5-di-tert-butyl-2-methylphenyl group with -CH(H)(OH) and C=O-O linkage] | resin | 73.25  8.45<br>73.33  8.50 | 100 |

TABLE 2-continued

| No. | Compound | m.p. (°C.) | C (%), H (%) (calcd/found) | Yield (%) |
|---|---|---|---|---|
| 202 | | 152–160 | 70.89  7.32<br>70.40  7.40 | 82 |
| 203 | | resin | characterised by<br>$^1$H-NMR (CDCl$_3$)<br>δ(H*) = 5.33 ppm | 45[a)] |
| 204 | | resin | characterised by<br>$^1$H-NMR (CDCl$_3$)<br>δ(H*) = 5.30 ppm | ~100 |
| 205 | | resin | characterised by<br>$^1$H-NMR (CDCl$_3$)<br>δ(H*) = 5.31 ppm | 98 |
| 206 | | resin | 71.03  7.95<br>71.10  7.98 | 92 |
| 207 | | resin | characterised by<br>$^1$H-NMR (CDCl$_3$)<br>δ(tert-butyl) = 1.34 ppm | ~100 |

TABLE 2-continued

| No. | Compound | m.p. (°C.) | C (%), H (%) (calcd/found) | Yield (%) |
|---|---|---|---|---|
| 208 | (3-tert-butyl-5-methylphenyl with α-chloro acetate substituent) | 81–86 | characterised by $^1$H-NMR (CDCl$_3$) δ(H*) = 5.34 ppm | 13 |
| 209 | (3-tert-butyl-5-(2-carboxyethyl)phenyl with α-hydroxy acetate substituent) | resin | characterised by $^1$H-NMR (CDCl$_3$) δ(H*) = 5.29 ppm | ~100 |
| 210 | (3-(1-methyl-1-phenylethyl)-5-(2-phenylpropan-2-yl)phenyl with α-hydroxy acetate substituent) | resin | characterised by $^1$H-NMR (CDCl$_3$) δ(H*) = 5.08 ppm | 38 |
| 211 | (3-neopentyl-5-methylphenyl with α-hydroxy acetate substituent) | 100–103 | 73.88  8.75<br>73.73  8.75 | 61 |
| 212 | (3-tert-butyl-5-methylphenyl with α-(methylcarbamoyloxy) acetate substituent) | 138–143 | 64.97  6.91<br>65.02  6.89 | 65 |

$^{a)}$chromatographed on silica gel (CH$_2$Cl$_2$/hexane = 4:1)

EXAMPLE 14

Stabilisation of multiple-extruded polypropylene 1.3 kg of polypropylene powder (Profax 6501), which has been prestabilised with 0.025% of Irganox® 1076 (n-octadecyl 3-[3,5-di-tert-butyl-4-hydroxyphenyl] propionate (melt index 3.2 g/10 min, measured at 230° C./2.16 kg) are blended with 0.05% of Irganox® 1010 (pentaerythritol tetrakis[3-(3,5-di-tert-butyl-4-hydroxyphenyl)propionate), 0.05% of calcium stearate, 0.03% of DHT 4A® Kyowa Chemical Industry Co., Ltd., [Mg$_{4.5}$Al$_2$(OH)$_{13}$CO$_3$.3,5H$_2$O]) and 0.5% of compound of Table 1. This blend is then extruded in an extruder having a cylinder diameter of 20 mm and a length of 400 mm at 100 rpm, the 3 heating zones being adjusted to the following temperatures: 260°, 270°, 280° C. The extrudate is cooled by drawing it through a water bath and is then granulated. This granulate is repeatedly extruded. After 3 extrusions, the melt index is measured (at 230° C./2.16 kg). A substantial increase in the melt index denotes pronounced chain degradation, i.e. poor stabilisation. The results are shown in Table 3.

TABLE 3

| Compound of Table 1 | Melt index after 3 extrusions |
|---|---|
| — | 17.1 |
| 103 | 4.8 |
| 104 | 5.0 |
| 105 | 4.9 |
| 106 | 4.9 |

EXAMPLE 15

Stabilisation of polyethylene during processing 100 parts of polyethylene powder (Lupolen® 5260 Z) are blended with 0.05 part of Irganox® 1010 (pentaerythritol tetrakis[3-(3,5-di-tert-butyl-4-hydroxyphenyl)propionate]) and 0.05 part of a compound of Table 1 and the blend is kneaded in a Brabender plastograph at 220° C. and 50 rpm. During this time the kneading resistance is recorded continuously as torque. In the course of the kneading time the polymer begins to crosslink after prolonged constancy, as can be determined by the rapid increase in torque. The time taken until a marked increase in torque is shown in Table 4 as a measure of the stabilising action. The longer this time is the better the stabilising action.

TABLE 4

| Compound of Table 1 | Time until increase in torque (min) |
|---|---|
| — | 9.5 |
| 103 | 27.0 |
| 107 | 26.0 |

EXAMPLE 16

Stabilisation of multiple-extruded polypropylene at high temperature 1.5 kg of polypropylene powder (Profax 6501), which has been prestabilised with 0.008% of Irganox® 1076 (n-octadecyl 3-[3,5-di-tert-butyl-4-hydroxyphenyl] propionate (melt index 3.2 g/10 min, measured at 230° C./2.16 kg) are blended with 0.05% of Irganox® 1010 (pentaerythritol tetrakis[3-(3,5-di-tert-butyl-4-hydroxyphenyl)propionate), 0.10% of calcium stearate and 0.015 to 0.100% of stabiliser or stabiliser mixture according to Table 5. This blend is then extruded in an extruder having a cylinder diameter of 20 mm and a length of 400 mm at 100 rpm, the 3 heating zones being adjusted to the following temperatures: 280°, 320°, 340° C. The extrudate is cooled by drawing it through a water bath and is then granulated. This granulate is repeatedly extruded. After 5 extrusions, the melt index is measured (at 230° C./2.16 kg). A substantial increase in the melt index denotes pronounced chain degradation, i.e. poor stabilisation. The results are shown in Table 5.

TABLE 5

| Stabiliser or mixture of stabilisers | Conzentration in % by weight | Melt index after 5 extrusions | | |
|---|---|---|---|---|
| | | 280° C. | 320° C. | 340° C. |
| ® Irgafos 168[a)] | 0.100 | 9.2 | 43.7 | 79.3 |
| ® Irgafos P-EPQ[b)] | 0.050 | 6.1 | 23.4 | 61.0 |
| Example 11[c)] | 0.015 | 8.5 | 19.7 | 23.6 |
| ® Irgafos 168[a)] | 0.045 | 7.3 | 24.4 | 26.7 |
| Example 11[c)] | 0.005 | | | |
| ® Irgafos P-EPQ[b)] | 0.045 | 5.6 | 15.7 | 23.6 |
| Example 11[c)] | 0.005 | | | |

[a)] ® Irgafos 168 is tris(2,4-di-tert-butylphenyl)phosphite.
[b)] ® Irgafos P-EPQ is tetrakis(2,4-di-tert-butylphenyl)4,4'-biphenylene diphosphonite.
[c)] Example 11 of the present application describes a mixture of c. 85% of 3-(3,4-di-methylphenyl)-5,7-di-tert-butyl-3H-benzofuran-2-one (compound (103), Table 1) as well as c. 15% of the 3-(2,3-dimethylphenyl)-5,7-di-tert-butyl-3H-benzofuran-2-one isomer (compound (103A)).

What is claimed is:
1. A compound of formula I

(I)

wherein $R_1$ is thienyl, benzo[b]thienyl, naphtho[2,3-b] thienyl, each unsubstituted or substituted by $C_1$–$C_4$ alkyl, $C_1$–$C_4$ alkoxy, $C_1$–$C_4$ alkylthio, hydroxy, halogen, amino, $C_{1-4}$ alkylamino, phenylamino or di($C_1$–$C_4$alkyl)amino;

$R_2$, $R_3$, $R_4$, and $R_5$ are each independently of one another hydrogen, chloro, hydroxy, $C_1$–$C_{25}$ alkyl, $C_7$–$C_9$ phenylalkyl, unsubstituted or $C_1$–$C_4$ alkyl-substituted phenyl, unsubstituted or $C_1$–$C_4$ alkyl-substituted $C_5$–$C_8$ cycloalkyl; $C_1$–$C_{18}$ alkoxy, $C_1$–$C_{18}$ alkylthio, $C_1$–$C_4$alkylamino, di($C_1$–$C_4$alkyl)amino, $C_1$–$C_{25}$ alkanoyloxy, $C_1$–$C_{25}$ alkanoylamino, $C_3$–$C_{25}$ alkenoyloxy, $C_3$–$C_{25}$ alkanoyloxy which is interrupted by oxygen, sulfur or >N—$R_{14}$, $C_6$–$C_9$ cycloalkylcarbonyloxy, benzoyloxy or $C_1$–$C_{12}$ alkyl-substituted benzoyloxy; or each pair of substituents $R_2$ and $R_3$ or $R_3$ and $R_4$ or $R_4$ and $R_5$, together with the linking carbon atoms, forms a benzene ring, Rd is additionally —$(CH_2)_p$—$COR_{15}$ or —$(CH_2)_q$OH;

$R_{14}$ is hydrogen or $C_1$–$C_8$ alkyl;
$R_{15}$ is hydroxy, $$\left( -O-\frac{1}{r} M^{r+} \right),$$

$C_1$–$C_{18}$ alkoxy or $$-N\begin{array}{c} R_{24} \\ R_{25} \end{array}$$

$R_{24}$ and $R_{25}$ are each independently of the other hydrogen or $C_1$–$C_{18}$ alkyl,
M is a metal cation of valency $r_1$
p is 0, 1 or 2;
q is 1, 2, 3, 4, 5 or 6;

r is 1, 2, or 3; and $R_8$ is hydrogen.

2. A compound according to claim 1, wherein $R_1$ is thienyl, unsubstituted or substituted by $C_1$–$C_4$ alkyl, $C_1$–$C_4$ alkoxy, $C_1$–$C_4$ alkylthia, hydroxy, halogen, amino, $C_1$–$C_4$ alkylamino or di($C_1$–$C_4$ alkyl) amino, $R_{15}$ is hydroxy, $C_1$–$C_{12}$ alkoxy or

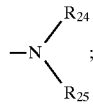

; and $R_{24}$ and $R_{25}$ are each independently of the other hydrogen or $C_1$–$C_{12}$ alkyl.

3. A compound according to claim 1, wherein $R_2$, $R_3$, $R_4$ and $R_5$ are each independently of one another hydrogen, chloro, $C_1$–$C_{18}$ alkyl, benzyl, phenyl, $C_5$–$C_8$ cycloalkyl, $C_1$–$C_{18}$ alkoxy, $C_1$–$C_{18}$ alkylthio, $C_1$–$C_{18}$ alkanoxyloxy, $C_1$–$C_{18}$ alkanoylamino, $C_3$–$C_{18}$ alkenoyloxy or benzoyloxy; or each pair of substituents $R_2$ and $R_3$ or $R_3$ and $R_4$ or $R_4$ and $R_5$, together with the linking carbon atoms, forms a benzene ring, $R_4$ is additionally —$(CH_2)_p$—$COR_{15}$ or —$(CH_2)_q$OH;

$R_{15}$ is hydroxy, $C_1$–$C_{12}$ alkoxy or

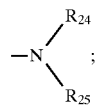

$R_{24}$ and $R_{25}$ are each independently of the other hydrogen or $C_1$–$C_{12}$ alkyl, p is 1 or 2, and q is 2, 3, 4, 5 or 6.

4. A compound according to claim 1, wherein at least two of $R_2$, $R_3$, $R_4$ and $R_5$ are hydrogen.

5. A compound according to claim 1, wherein $R_3$ and $R_5$ are hydrogen.

6. A compound according to claim 1 wherein $R_2$ and $R_4$ are $C_1$–$C_4$ alkyl and $R_3$ and $R_5$ are hydrogen.

* * * * *